(12) United States Patent
DeRosa-Grund

(10) Patent No.: US 11,996,174 B2
(45) Date of Patent: May 28, 2024

(54) BLOCKCHAIN ARCHITECTURE, SYSTEM, METHOD AND DEVICE FOR FACILITATING ELECTRONIC HEALTH RECORD MAINTENANCE, SHARING AND MONETIZATION USING A DECENTRALIZED HEALTH INFORMATION PLATFORM INCLUDING A NON-FUNGIBLE TOKEN FUNCTION AND SECURITY PROTOCOLS

(71) Applicant: Atrium Separate IP Holdings Number 1, LLC, Sheridan, WY (US)

(72) Inventor: H. Anthony DeRosa-Grund, Magnolia, TX (US)

(73) Assignee: Atrium Separate IP Holdings Number 4, LLC, Sheridan, WY (US)

( * ) Notice: Subject to any disclaimer, the term of this patent is extended or adjusted under 35 U.S.C. 154(b) by 54 days.

(21) Appl. No.: 17/742,594

(22) Filed: May 12, 2022

(65) Prior Publication Data

US 2022/0270725 A1    Aug. 25, 2022

Related U.S. Application Data

(63) Continuation-in-part of application No. 17/483,604, filed on Sep. 23, 2021, which is a continuation-in-part
(Continued)

(51) Int. Cl.
*G06F 16/00* (2019.01)
*G06F 21/60* (2013.01)
(Continued)

(52) U.S. Cl.
CPC ........... *G16H 10/60* (2018.01); *G06F 21/602* (2013.01); *G06F 21/6245* (2013.01); *G06Q 30/0645* (2013.01)

(58) Field of Classification Search
CPC ..... H04L 9/50; H04L 9/3239; H04L 2209/56; H04L 9/3213; H04L 9/30; H04L 9/3234;
(Continued)

(56) References Cited

U.S. PATENT DOCUMENTS 10,521,780 B1    12/2019  Hopkins, III
10,885,170 B1    1/2021   Maliani
(Continued)

OTHER PUBLICATIONS

Johnson, R.C. et al., "Secure Voice-Based authentication for mobile devices: vaulted voice verification. In Biometric and Surveillance Technology for Human and Activity Identification X",(vol. 8712,pp. 164-176) SPIW. (May 2013).
(Continued)

*Primary Examiner* — Shyue Jiunn Hwa
(74) *Attorney, Agent, or Firm* — Haverstock & Owens, A Law Corporation

(57) ABSTRACT

A distributed transaction and data storage platform including a distributed notary ledger, chain arrayed data store or blockchain and one or more individual user micro-identifier chains that together enable the secure effectuation, recordation and sharing of one or more transactions including electronic health record non-fungible tokens, and/or cyber-secured storage of data in an automated, real-time, zero-trust, globally data law and privacy law centric manner while maintaining transaction party confidentiality and preventing chain poisoning.

33 Claims, 11 Drawing Sheets

Related U.S. Application Data of application No. 17/322,217, filed on May 17, 2021, which is a continuation-in-part of application No. 17/188,609, filed on Mar. 1, 2021, which is a continuation-in-part of application No. 17/025,888, filed on Sep. 18, 2020, which is a continuation-in-part of application No. 16/855,918, filed on Apr. 22, 2020, now Pat. No. 11,507,948.

(60) Provisional application No. 63/188,300, filed on May 13, 2021, provisional application No. 63/082,383, filed on Sep. 23, 2020.

(51) Int. Cl.
*G06F 21/62* (2013.01)
*G06Q 30/0645* (2023.01)
*G16H 10/60* (2018.01)

(58) Field of Classification Search
CPC ..... H04L 9/0643; H04L 9/3218; G06F 21/74; G06F 21/602; G06F 16/2365; G06F 21/64; G06F 16/2379; G06F 16/27; G06F 16/9024; G06F 1/163; G06F 16/90332; G06F 16/9536; G06F 1/1694; G06F 2203/011; G06F 2203/0384; G06F 3/00; G06F 3/011; G06F 3/012; G06F 3/013; G06F 3/014; G06F 3/017
See application file for complete search history.

(56) References Cited

U.S. PATENT DOCUMENTS

| | | |
|---|---|---|
| 11,049,128 B1 | 6/2021 | Olson |
| 2016/0092988 A1 | 3/2016 | Letourneau |
| 2016/0217532 A1 | 7/2016 | Slavin |
| 2017/0048230 A1 | 2/2017 | Johansson |
| 2017/0171580 A1 | 6/2017 | Hirsch |
| 2017/0300872 A1 | 10/2017 | Brown |
| 2017/0345011 A1 | 11/2017 | Salami |
| 2017/0352012 A1 | 12/2017 | Hearn |
| 2018/0308134 A1 | 10/2018 | Manning |
| 2018/0323963 A1 | 11/2018 | Stollman |
| 2019/0026821 A1 | 1/2019 | Bathen |
| 2019/0034975 A1 | 1/2019 | Rizk |
| 2019/0058581 A1 | 2/2019 | Wood |
| 2019/0130416 A1 | 5/2019 | Boudville |
| 2019/0149600 A1 | 5/2019 | Duan |
| 2019/0220603 A1 | 7/2019 | Gopalakrishnan |
| 2019/0251527 A1 | 8/2019 | Surdak |
| 2019/0340623 A1 | 11/2019 | Rivkind |
| 2019/0354725 A1 | 11/2019 | Lowagie |
| 2019/0363890 A1 | 11/2019 | Johnson |
| 2019/0370866 A1 | 12/2019 | Lawbaugh |
| 2019/0385215 A1 | 12/2019 | Ferenczi |
| 2020/0042773 A1 | 2/2020 | Benkreira et al. |
| 2020/0051041 A1 | 2/2020 | Ko |
| 2020/0051368 A1 | 2/2020 | Pustizzi |
| 2020/0058023 A1 | 2/2020 | Travizano |
| 2020/0065922 A1 | 2/2020 | Goldstaj |
| 2020/0076827 A1 | 3/2020 | Gluck |
| 2020/0118124 A1 | 4/2020 | Menon |
| 2020/0175003 A1 | 6/2020 | Jiang |
| 2020/0186962 A1 | 6/2020 | Moeller |
| 2020/0210413 A1 | 7/2020 | Quick |
| 2020/0213121 A1* | 7/2020 | Hioki ............... H04L 9/3239 |
| 2020/0213329 A1* | 7/2020 | Simons ............. H04L 9/3226 |
| 2020/0236032 A1 | 7/2020 | Singla |
| 2020/0242595 A1 | 7/2020 | Harrison |
| 2020/0267163 A1 | 8/2020 | Wilson |
| 2020/0320220 A1 | 10/2020 | Beno |
| 2020/0334752 A1* | 10/2020 | Doney ............. G06Q 20/3672 |
| 2020/0351094 A1* | 11/2020 | Canterbury ......... H04L 9/0637 |
| 2021/0049608 A1 | 2/2021 | Yang |
| 2021/0182423 A1 | 6/2021 | Padmanabhan |
| 2021/0351939 A1 | 11/2021 | Wang |
| 2022/0123945 A1 | 4/2022 | Yang |

OTHER PUBLICATIONS

Chang, Y.T. et al., "My Voiceprint is my authenticator: A two-layer authentication approach using voiceprint for voice assistants", (Aug. 2019).

* cited by examiner

```
type Transaction struct {          ─ 802
        Header      TxHeader       ─ 804
        Payload     TxPayload
        Signature   TxSignature
        Hash        [ 16 ] byte    ── 806
}                                  ── 808 type TxHeader struct {
        TransactionType        TransactionType
        TransactionSubject     [] byte // e.g., Smart Contract to Execute
        TransactionTarget      [] byte // e.g., Party B in Contract
        SubjectType            SubjectType
        SubjectOtherMidcOwner  [ 33 ] byte                                   ─ 802
        PubKey                 [ 33 ] byte
        NotaryPubKey           [ 49 ] byte
        GeneratedAt            time.Time
} type TxPayload struct {    ─ 804
        Data   [] byte
} type TxSignature struct {
        Signature string              ─ 806
        NotarySignature string
} type SubjectType int const (
        STSelf        SubjectType = 0
        STNotary      SubjectType = 1   ─ 810
        STOtherMidc   SubjectType = 2
)
```

Fig. 8A

```
type Transaction struct {                    ─ 802
        Header      TxHeader   ─── 804
        Payload     TxPayload ─┘
        Signature   TxSignature ─┐
        Hash        [ 32 ] byte ─┴─ 806
}                                 └─ 808 type TxHeader struct {
        TransactionType      TransactionType
        TransactionSubject   [] byte
        TransactionTarget    [] byte
        SubjectType          SubjectType
        SubjectMidcOwner     [ 33 ] byte       ⎬ 802
        OriginatorTx         [ 16 ] byte
        OriginatorMidc       [ 33 ] byte
        PubKey               [ 49 ] byte
        GeneratedAt          time.Time
}
                           ─ 804
type TxPayload struct {
Data [] byte
} type TxSignature struct {      ⎫
        Signature string       ⎬ 806
}                              ⎭ type SubjectType int const (   ⎫
        STNotary   SubjectType = 0   ⎬ 810
        STMidc     SubjectType = 1   ⎭
)
```

Fig. 8B

BLOCKCHAIN ARCHITECTURE, SYSTEM, METHOD AND DEVICE FOR FACILITATING ELECTRONIC HEALTH RECORD MAINTENANCE, SHARING AND MONETIZATION USING A DECENTRALIZED HEALTH INFORMATION PLATFORM INCLUDING A NON-FUNGIBLE TOKEN FUNCTION AND SECURITY PROTOCOLS

RELATED APPLICATIONS

This patent application claims priority under 35 U.S.C. 119(e) of the co-pending U.S. Provisional Patent Application No. 63/188,300, filed May 13, 2021, entitled "A BLOCKCHAIN ARCHITECTURE, SYSTEM, METHOD AND DEVICE FOR FACILITATING ELECTRONIC HEALTH RECORD MAINTENANCE, SHARING AND MONETIZATION USING A DECENTRALIZED HEALTH INFORMATION PLATFORM INCLUDING A NON-FUNGIBLE TOKEN FUNCTION AND SECURITY PROTOCOLS."

Additionally, this patent application is a continuation-in-part of the co-pending U.S. patent application Ser. No. 17/483,604, filed Sep. 23, 2021, and entitled "A BLOCKCHAIN ARCHITECTURE, SYSTEM, METHOD AND DEVICE INCLUDING A HYBRID PUBLIC-PRIVATE ITERATION FOR FACILITATING SECURE DATA COLLECTION AND CONTROLLED DISTRIBUTION USING A DECENTRALIZED TRANSACTION INFORMATION PLATFORM AND TOKEN ECOSYSTEM," which is a continuation-in-part of the co-pending U.S. patent application Ser. No. 17/322,217, filed May 17, 2021, and entitled "A BLOCKCHAIN ARCHITECTURE, SYSTEM, METHOD AND DEVICE FOR AUTOMATED CYBERSECURITY AND DATA PRIVACY LAW COMPLIANCE WITH A STREAMLINED BLOCK STRUCTURE," which is a continuation-in-part of the co-pending U.S. patent application Ser. No. 17/188,609, filed Mar. 1, 2021, and entitled "A BLOCKCHAIN ARCHITECTURE, SYSTEM, METHOD AND DEVICE FOR AUTOMATED CYBERSECURITY AND DATA PRIVACY LAW COMPLIANCE WITH A STREAMLINED BLOCK STRUCTURE," which is a continuation-in-part of the co-pending U.S. patent application Ser. No. 17/025,888, filed Sep. 18, 2020, entitled "A BLOCKCHAIN ARCHITECTURE, SYSTEM, METHOD AND DEVICE FOR AUTOMATED CYBERSECURITY AND DATA PRIVACY LAW COMPLIANCE WITH A PARTITIONED REPLICATION PROTOCOL," which is a continuation-in-part of the co-pending U.S. patent application Ser. No. 16/855,918, filed Apr. 22, 2020, entitled "A BLOCKCHAIN ARCHITECTURE, SYSTEM, METHOD AND DEVICE FOR AUTOMATED CYBERSECURITY AND DATA PRIVACY LAW COMPLIANCE WITH DELAYED BLOCK POSTING PROTOCOL," all of which are hereby incorporated by reference.

Additionally, co-pending U.S. patent application Ser. No. 17/483,604, filed Sep. 23, 2021, and entitled "A BLOCKCHAIN ARCHITECTURE, SYSTEM, METHOD AND DEVICE INCLUDING A HYBRID PUBLIC-PRIVATE ITERATION FOR FACILITATING SECURE DATA COLLECTION AND CONTROLLED DISTRIBUTION USING A DECENTRALIZED TRANSACTION INFORMATION PLATFORM AND TOKEN ECOSYSTEM" claims priority under 35 U.S.C. 119(e) of U.S. Provisional Patent Application No. 63/082,383, filed Sep. 23, 2020, entitled "A BLOCKCHAIN ARCHITECTURE, SYSTEM, METHOD AND DEVICE FOR FACILITATING SECURE MEDICAL TESTING, DATA COLLECTION AND CONTROLLED DISTRIBUTION USING A DECENTRALIZED HEALTH INFORMATION PLATFORM AND TOKEN ECOSYSTEM."

FIELD OF THE INVENTION

The present invention relates to the field of distributed ledger and blockchain systems. More particularly, the present invention relates to the sharing of electronic heath records using an interoperating distributed ledger and blockchain systems.

BACKGROUND OF THE INVENTION

Health data, and in particular electronic health records) are a unique and inordinately valuable asset. Health data is the new "oil." It can be copied and disseminated quickly, unlike traditional physical assets, which can be controlled by one entity at a time. They are unique (nobody is the same, and no combination is the same), additive (more data enable better understanding of the characteristics and strong statistical power in hypothesis testing), non-depletive (they are not a consumable resource) and replicable (as a digital resource that can be copied to numerous parties quickly). Medical records are shared between providers and patients to provide necessary care and support the well-being of all society. Many companies—not just those in the health vertical—are keen to access personal health data.

Currently, doctors spend more time navigating patients' electronic health records (EHR) than they spend with the patients. Why? Because most countries have decades old laws mandating that medical providers must use and EHR systems of their choice. Physicians in different facilities cannot easily share patient data, imaging or lab results as most have different EHR systems whose records are not interoperable. Additionally, setup costs for a new EHR system can run providers well over $100,000 US and annual usage and maintenance fees can easily surpass that. As a result, patient care suffers as doctors have limited time with patients and limited information shared from other doctors and/or medical facilities.

At the same time, blockchains are plagued with problems that limit, and inhibit, its vast potential. These include inability to scale, limit to the number of transactions per second, security vulnerabilities, inefficiency, and costly and problematic consensus mechanisms. Additionally, they are by their very nature unable to be compliant with international data privacy laws, including, but not limited to the GDPR and CCPA. All data, including Private Personal Information, once placed on existing blockchains can never be removed. Blockchain's strength of immutability of data is also its weak point regarding compliance with regulatory and data privacy laws. Blockchain immutability renders all existing chains in perpetual violation of global data privacy laws as these laws give users, among other rights, the incontrovertible right to have their data removed from a chain upon their request.

SUMMARY OF THE INVENTION

A transaction platform including a notary distributed ledger or blockchain and one or more separate micro-identifier chains (MIDCs) that together enable the secure effectuation and recordation of one or more transactions and storage of data in an automated privacy and regulatory law compliant manner (with or without zero-trust) while maintaining transaction party confidentiality and preventing chain poisoning. The notary distributed ledgers or blockchains, as well as the MIDC's are able to use single transaction blocks to store, maintain and provide information about the parties related to the transactions which the blockchain is able to utilize in order to securely and quickly validate, execute and record the transactions. The single transaction blocks and distributed ledger, transaction and data store thereof is able to function as a public or private blockchain (e.g. a distributed blockchain or database across a plurality of computing devices that each store copies of transactions in one or more linked blocks, in this case single transaction blocks) that maintains a continuously-growing list of data records hardened against tampering and revision. In particular, unlike other blockchains where a single block is used to store thousands of transactions, the single transaction blockchain of this system is able to consist of data structure blocks with each block holding only one individual transaction, piece of data (e.g., document, audio file, video file, biometric characteristics, or other types of data) and/or the results of any blockchain executables. Each single transaction block of the blockchain is able to comprise a timestamp and information linking it to a previous block thereby defining the chain and maintaining an order of each of the records/transactions. Further, the blockchains are able to implement a partitioned RAFT replication protocol in order to distribute the recording workload and increase transaction throughput, processing speed and efficiency.

The native user data, as well as Private Personal Information (PPI) for each user is able to be stored on the micro-identifier chain. A plurality of MIDCs can be combined to form a micro-identifier chain arrays for the transaction platform. In some embodiments, MIDC stacked on top of each other look like a database in that they have rows, and columns. The single transaction blocks in each MIDC are the equivalent of cells in a database. This totality of these stacked MIDC combine together to form the distributed storage equivalent of a database that we call a Chain Arrayed Data Store. This Chained Arrayed Data Store and STB allow the system to emulate the CRUD (Create, Read, Update and Delete) of a database. As such it allows the system to be the only DLT or blockchain capable of modifying and or deleting data in such a manner not to compromise the integrity and immutability of the chain or DLT itself.

In some embodiments, the platform comprises a decentralized health information (DeHI) module or engine that uniquely enables users to convert their electronic health records (EHR) into non-fungible tokens (NFTs) that are able to be stored on their MIDCs and/or represented on the notary blockchain to ensure their authenticity. In particular, the DeHI module enables users to selectively share their electronic health records with medical providers and/or other entities as permitted by the user in exchange for compensation to the user and/or the platform. As a result, the module provides the improvement of ensuring the security and privacy of electronic health records while also enabling the records to be selectively shared with one or more entities in order to both keep the records up to date as well as to enable the users to receive payment for the sharing of their medical data. In some embodiments, the platform may be used for a private permissioned blockchain, or a hybrid public-private chain with a cryptocurrency component.

A first aspect is directed to an electronic health record blockchain platform for sharing electronic health records of a plurality of users having accounts on the platform. The platform comprises a non-transitory computer-readable memory cluster storing a micro-identification blockchain array formed by a stack of a plurality of micro-identification blockchains, wherein at least one of the micro-identification blockchains is dedicated to a user of the users, a user device including a user device processor and a user device non-transitory memory storing a health application, wherein when executed by the user device processor the health application is operable to input electronic health data of the user, enable the user to select a portion of the electronic health data for token generation, generate an electronic health record non-fungible token (EHRNFT) based on the selected portion of the electronic health data, the EHRNFT including a token identifier and the selected portion, store the EHRNFT on the micro-identification blockchain dedicated to the user as a single block separate from any existing blocks of the micro-identification blockchain, enable the user to give permission to one or more entities to access the EHRNFT, provide access to the portion of the EHRNFT upon receiving input of the permission from the user and remove the access to the portion of the EHRNFT upon a termination of the permission.

In some embodiments, the health information includes one or more current medical conditions of the user and a medical history of the user. In some embodiments, the platform further comprises an entity device including an entity device processor and an entity device non-transitory memory storing the health application, wherein when executed by the entity device processor the health application is operable to enable a provider to transmit a heath record request message to the user device, the request message including an identifier of the user and the token identifier and enable the provider to submit payment to the user for access to the EHRNFT identified by the token identifier. In some embodiments, the enabling the user to give permission to one or more entities to access the EHRNFT comprises communicating a permission confirmation message to the user on the user device in response to receiving the health record request message. In some embodiments, the enabling the user to give permission to one or more entities to access the EHRNFT comprises displaying a set of available entities to the user on the user device and receiving selection by the user of the one or more entities from the set. In some embodiments, the termination of the permission comprises an expiration of a rental period associated with the EHRNFT. In some embodiments, the health application is operable to extend the rental period upon receipt of payment from the provider.

In some embodiments, when executed by the user device processor the health application is operable to enable input of updated electronic health data, enable the user to select another portion of the updated electronic health data for token generation, generate an updated EHRNFT based on the another portion of the updated electronic health data, the updated EHRNFT including another token identifier and the another portion and store the another EHRNFTs on the micro-identification blockchain dedicated to the user on another separate block. In some embodiments, when executed by the entity device processor the health application is operable to enable the provider to input the updated electronic health data. In some embodiments, when executed by the user device processor the health application is operable to enable the user to select one or more additional portions of the electronic health data for token generation, generate an additional EHRNFT for each of the additional portions based on the additional portion of the electronic health data, the additional EHRNFTs each including an additional token identifier and the additional portion and store each of the additional EHRNFTs on the micro-identification blockchain dedicated to the user on a separate additional block. In some embodiments, the token identifier is a hash of the selected portion of the electronic health data.

Another aspect is directed to a non-transitory computer-readable medium of a device storing a health application, wherein when executed by a device processor the health application is operable to input electronic health data of the user, enable the user to select a portion of the electronic health data for token generation, generate an electronic health record non-fungible token (EHRNFT) based on the selected portion of the electronic health data, the EHRNFT including a token identifier and the selected portion, store the EHRNFT on a micro-identification blockchain dedicated to the user as a single block separate from any existing blocks of the micro-identification blockchain, the micro-identification blockchain stored on a non-transitory computer-readable memory cluster, enable the user to give permission to one or more entities to access the EHRNFT, provide access to the portion of the EHRNFT upon receiving input of the permission from the user and remove the access to the portion of the EHRNFT upon a termination of the permission.

In some embodiments, the health information includes one or more current medical conditions of the user and a medical history of the user. In some embodiments, when executed by the device processor the health application is operable to enable a provider to transmit a heath record request message to the user, the request message including an identifier of the user and the token identifier and enable the provider to submit payment to the user for access to the EHRNFT identified by the token identifier. In some embodiments, the enabling the user to give permission to one or more entities to access the EHRNFT comprises communicating a permission confirmation message to the user on the user device in response to receiving the health record request message. In some embodiments, the enabling the user to give permission to one or more entities to access the EHRNFT comprises displaying a set of available entities to the user on the device and receiving selection by the user of the one or more entities from the set. In some embodiments, the termination of the permission comprises an expiration of a rental period associated with the EHRNFT. In some embodiments, the health application is operable to extend the rental period upon receipt of payment from the provider.

In some embodiments, when executed by the device processor the health application is operable to enable input of updated electronic health data, enable the user to select another portion of the updated electronic health data for token generation, generate an updated EHRNFT based on the another portion of the updated electronic health data, the updated EHRNFT including another token identifier and the another portion and store the another EHRNFTs on the micro-identification blockchain dedicated to the user on another separate block. In some embodiments, when executed by the device processor the health application is operable to enable the provider to input the updated electronic health data. In some embodiments, when executed by the device processor the health application is operable to enable the user to select one or more additional portions of the electronic health data for token generation, generate an additional EHRNFT for each of the additional portions based on the additional portion of the electronic health data, the additional EHRNFTs each including an additional token identifier and the additional portion and store each of the additional EHRNFTs on the micro-identification blockchain dedicated to the user on a separate additional block. In some embodiments, the token identifier is a hash of the selected portion of the electronic health data.

Another aspect is directed to a method of sharing electronic health data of a plurality of users using a micro-identification blockchain array formed by a stack of a plurality of micro-identification blockchains, wherein at least one of the micro-identification blockchains is dedicated to a user of the users. The method comprises with a user device having a processor and a non-transitory computer-readable memory storing a health application inputting electronic health data of the user, enabling the user to select a portion of the electronic health data for token generation, generating an electronic health record non-fungible token (EHRNFT) based on the selected portion of the electronic health data, the EHRNFT including a token identifier and the selected portion, storing the EHRNFT on the micro-identification blockchain dedicated to the user as a single block separate from any existing blocks of the micro-identification blockchain, enabling the user to give permission to one or more entities to access the EHRNFT, providing access to the portion of the EHRNFT upon receiving input of the permission from the user and removing the access to the portion of the EHRNFT upon a termination of the permission.

In some embodiments, the health information includes one or more current medical conditions of the user and a medical history of the user. In some embodiments, the method further comprises, with an entity device storing the health application, enabling a provider to transmit a heath record request message to the user device, the request message including an identifier of the user and the token identifier and enabling the provider to submit payment to the user for access to the EHRNFT identified by the token identifier. In some embodiments, the enabling the user to give permission to one or more entities to access the EHRNFT comprises communicating a permission confirmation message to the user on the user device in response to receiving the health record request message. In some embodiments, the enabling the user to give permission to one or more entities to access the EHRNFT comprises displaying a set of available entities to the user on the user device and receiving selection by the user of the one or more entities from the set. In some embodiments, the termination of the permission comprises an expiration of a rental period associated with the EHRNFT. In some embodiments, the health application is operable to extend the rental period upon receipt of payment from the provider.

In some embodiments, the method further comprises, with the user device, enabling input of updated electronic health data, enabling the user to select another portion of the updated electronic health data for token generation, generating an updated EHRNFT based on the another portion of the updated electronic health data, the updated EHRNFT including another token identifier and the another portion and storing the another EHRNFTs on the micro-identification blockchain dedicated to the user on another separate block. In some embodiments, when executed by the entity device processor the health application is operable to enable the provider to input the updated electronic health data. In some embodiments, the method further comprises, with the user device, enabling the user to select one or more additional portions of the electronic health data for token generation, generating an additional EHRNFT for each of the additional portions based on the additional portion of the electronic health data, the additional EHRNFTs each including an additional token identifier and the additional portion and storing each of the additional EHRNFTs on the micro-identification blockchain dedicated to the user on a separate additional block. In some embodiments, the token identifier is a hash of the selected portion of the electronic health data.

BRIEF DESCRIPTION OF THE DRAWINGS

FIG. 8A illustrates an exemplary transaction that is able to be used in the MIDC chain according to some embodiments.

FIG. 8B illustrates an exemplary transaction that is able to be used in the notary chain according to some embodiments.

DETAILED DESCRIPTION OF THE INVENTION

Embodiments are directed to a transaction platform including a notary distributed ledger or blockchain and one or more separate micro-identifier chains (MIDCs) that together enable the secure effectuation and recordation of one or more transactions while maintaining transaction party confidentiality and preventing chain poisoning. In some embodiments, the transactions include electronic heath record non-fungible tokens that are able to be selectively created, updated and shared. Further, in some embodiments the platform may be used for a private permissioned blockchain, or a hybrid public-private chain with a cryptocurrency component.

The notary distributed ledgers or blockchains are able to be a single transaction blockchain to store, maintain and provide information about the parties related to the transactions which the blockchain is able to utilize in order to securely and quickly validate, execute and record the transactions. The single transaction distributed blockchain is able to be a public or private blockchain (e.g. a distributed blockchain or database across a plurality of computing devices that each store copies of transactions in one or more linked blocks) that maintains a continuously-growing list of data records hardened against tampering and revision. In particular, unlike other blockchains where a single block is used to store thousands of transactions, the single transaction blockchain of this system is able to consist of data structure blocks with each block holding only one individual transaction and/or the results of any blockchain executables. Each block of the blockchain is able to comprise a timestamp and information linking it to a previous block thereby defining the chain and maintaining an order of each of the records/transactions.

The native user data for each user is able to be stored on the micro-identifier chain. A plurality of MIDCs can be combined to form a micro-identifier chain arrays for the transaction platform. In such embodiments, for each user, only a specified single transaction block of their micro-identification chain that stores de-identified user data is able to be accessed by the notary blockchain(s) in order to form on-chain transactions. The data stored on the notary chain (s), and the other single transaction blocks of the micro-identification chain(s) is kept secure from any intruders.

Blockchain Transaction System

Figure 1:
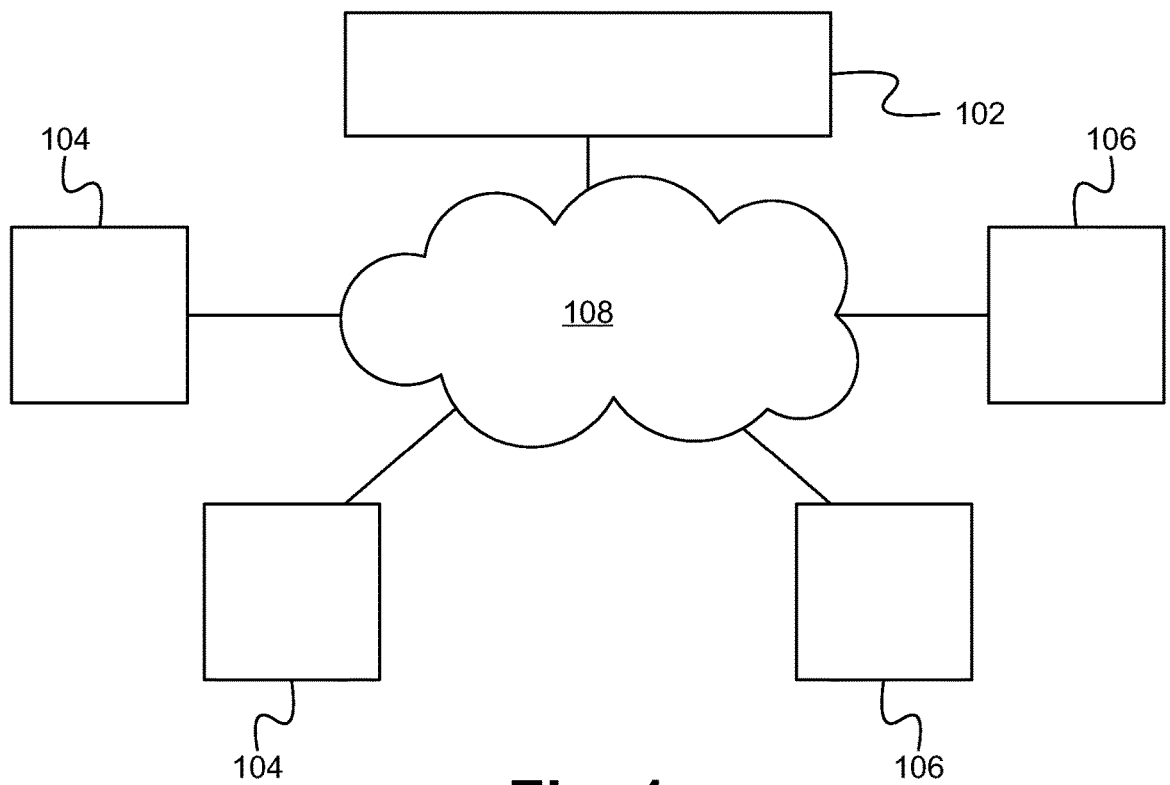
FIG. 1 illustrates a blockchain transaction system according to some embodiments.

FIG. 1 illustrates a blockchain transaction system 100 according to some embodiments. As shown in FIG. 1, the system 100 comprises a transaction platform 102 coupled with one or more buyer devices 104 and one or more seller devices 106 over one or more networks 108. The networks 108 are able to be one or a combination of wired or wireless networks as are well known in the art. Although as shown in FIG. 1 one transaction platform 102 is coupled with two buyer devices 104 and two seller devices 106, it is understood that the system 100 is able to comprise any number of platforms 102, buyers devices 104 and/or seller devices 106 coupled together via the network 108. Additionally, although described as buyer/seller devices 104, 106, it is understood that the devices 104, 106 are able to be devices of any users.

Figure 2:
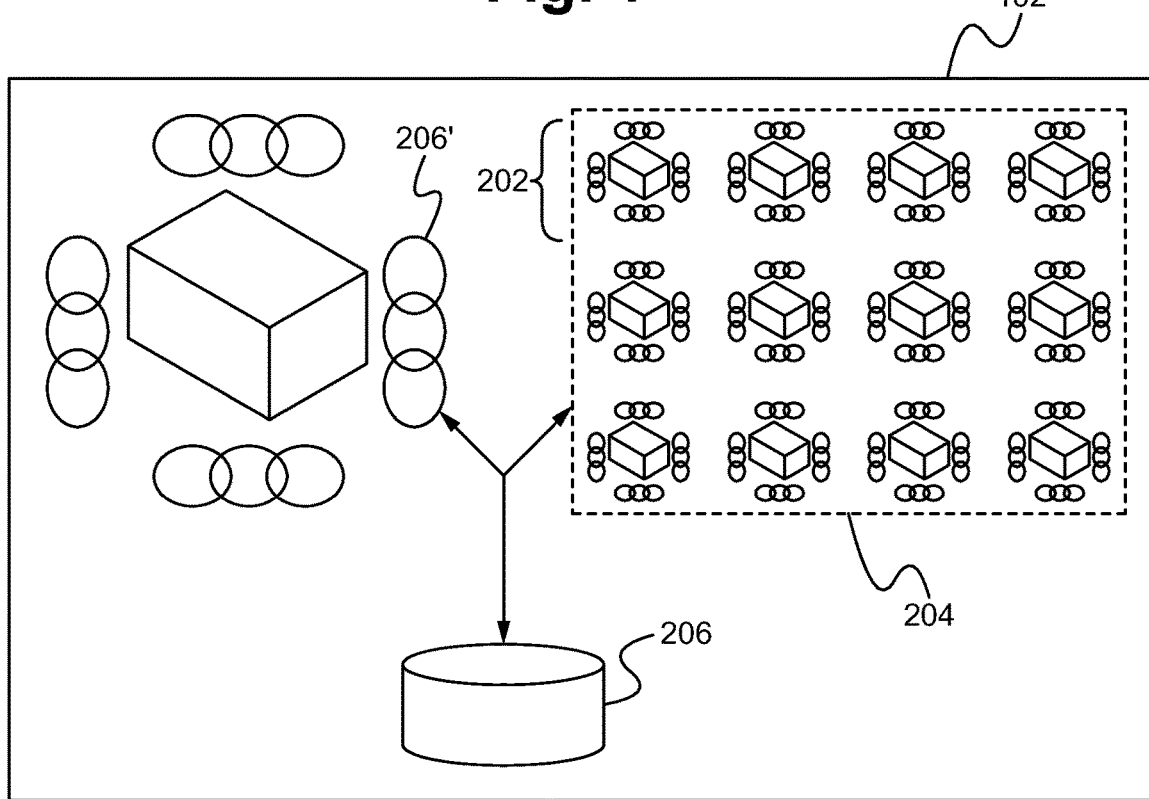
FIG. 2 illustrates a detailed view of the transaction platform according to some embodiments.

FIG. 2 illustrates a detailed view of the transaction platform 102 according to some embodiments. As shown in FIG. 2, the platform comprises a platform operating system 206 (e.g. including a plurality of separate modules/engines and stored on/operated by one or more physical servers or the cloud), one or more micro-identification chain (MIDC) arrays 204 formed by one or more a micro-identification chains 202, and at least one notary blockchain 206' (e.g. notary blockchain cluster(s) including a plurality of nodes each being operated by one or more node servers) all operably coupled together with the operating system 206 executing the functions described herein with and for arrays 204 and the blockchain 206'. In particular, the operating system 206 is able to comprise one or both of programming/code stored within the arrays 204 and/or blockchain 206' and programming/code stored outside the arrays 204 and/or blockchain 206' (e.g. within the one or more physical servers or the cloud). Further, in some embodiments the operating system 206 is able to be secure operating systems utilizing encryption in order to protect stored data. In some embodiments, the platform 102 comprises separate MIDC arrays 204 for seller MIDCs and buyer MIDCs. Alternatively, the seller and buyer MIDCs are able to be a part of the same array 204 (e.g. a user MIDC array 204). The operating system 206, arrays 204 and the notary blockchain 206' are able to be coupled together over the network 108 (and/or other networks).

In some embodiments, the platform 102 includes one or more side chains coupled between blockchains of the operating system 206 and/or the MIDC arrays 204. Specifically, the sidechains are able to be mechanisms that allow tokens and other digital assets from one blockchain to be securely used in a separate blockchain and then be moved back to the original blockchain if needed. In other words, the pegged sidechains are a blockchain that is attached to the parent chain (notary blockchain) through the two-way peg mechanism which allows bidirectional transfer of assets between the parent chain and the sidechain at a fixed deterministic exchange rate by using a separate token currency tied to the parent chain. In such embodiments, by using a two-way peg mechanism, the unauthorized creation of tokens and sidechains is precluded. Alternatively, the side chains are able to be omitted and/or application programming interfaces (APIs) may be used by the system to effectuate inter-chain and/or inter-ledger operability.

The notary blockchain 206' is able to be a public/private hybrid blockchain (or a public blockchain or a private permissioned blockchain). For example, the blocks of the blockchain 206' are able to only be viewed by a permissioned user (e.g. having a valid account on the system 100 using the encoder/decoder/view module "Rosetta" described below). The each of the blocks of the blockchain 206' are able to store a single transaction between one or more users (e.g. a seller and a buyer) and indicate the details of the transaction (as described below) including identifiers of the MIDCs 202 of the users that are a party to the transaction. In some embodiments, a single transaction block is created on the notary chain 206' for pending transactions (e.g. pending transaction blocks) and then a subsequent single transaction block is created when/if the transactions are completed (e.g. completed transaction blocks).

In some embodiments, the notary blockchain 206' is plasma network blockchain and smart contract platforms featuring on-chain, off-chain and/or cross-chain atomic swaps, lightning network functionality, two-way pegged sidechains and/or instant payments. In some embodiments, the platform operating system 206 comprises (e.g. native) smart contracts which are automated smart contracts each containing a set of rules under which the advertiser, the platform and the user have already agreed that when the rules are met, the agreement is automatically enforced. Specifically, the smart contract code facilitates, verifies and enforces the performance of that agreement and results in a transaction, and smart contract, that is saved to the notary blockchain 206' and/or the MIDCs 202 of the associated buyers/sellers, where proportional pre-determined amounts from the proceeds of the transaction (as specified in the contract) are directed to the user, the platform and/or other entities. Alternatively, one or more of the notary blocks are able to not include smart contracts (e.g. be just data blocks).

Figure 5:
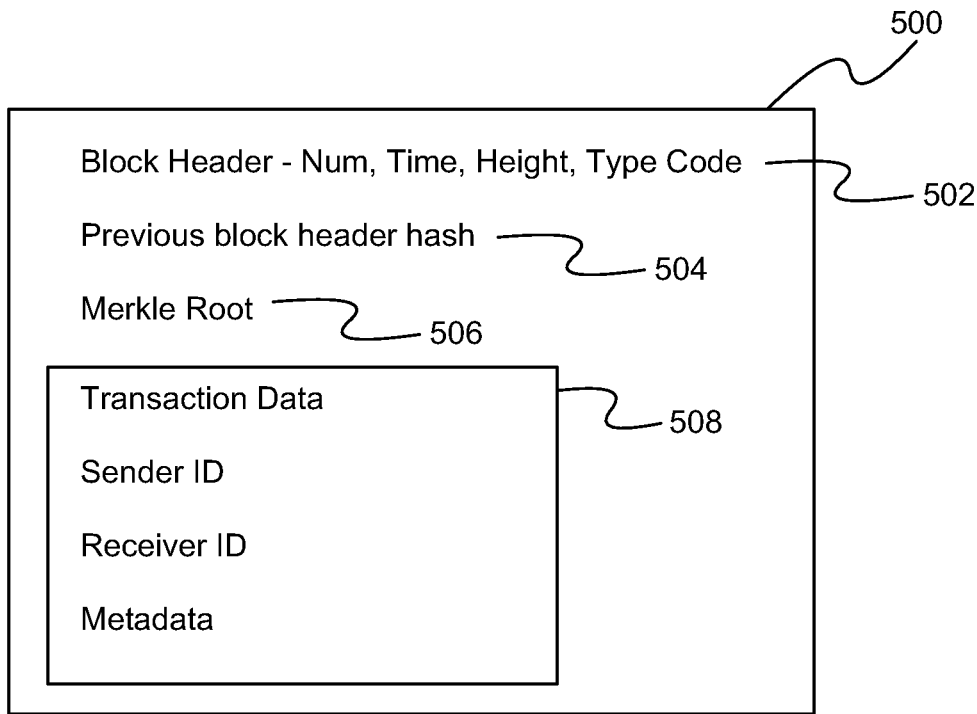
FIG. 5 illustrates an exemplary transaction block according to some embodiments.

FIG. 5 illustrates an exemplary notary blockchain 206' and/or MIDC 202 transaction block 500 according to some embodiments. As shown in FIG. 5, the single transaction block 500 comprises a block header 502 including a block number, a time of creation, a block height, a block type value and/or other values. Types of single transaction blocks found on the notary blockchain 206' and/or MIDCs 202 include, but are not limited to, genesis PPI blocks, updates to PPI blocks, pending transaction blocks, completed transaction blocks, pending dispute blocks, completed dispute blocks and/or other types of blocks. Each of the types are able to have a different corresponding type code such that the value of the type code in the header 502 of the block indicates what type of block it is. As further shown in FIG. 5, the block 500 is also able to comprise a hash 504 of the header of the previous block in the chain, a merkle root value 506 and block type-specific data 508. Unlike prior art blocks, the transaction block 500 is able to omit a transaction count value. Specifically, because the system 100 utilizes only a single transaction per block 500, there is no need for a transaction count value to be included in the block 500 as the value will always be just one. Similarly, in some embodiments the block 500 is able to omit the merkle root value 506 as only a single transaction is stored on the block 500 so it is not necessary to store a merkle root value 506 describing the structure of how the single transaction is stored on the block 500.

Additionally, because the block 500 shown in FIG. 5 is a transaction block, the block type-specific data 508 is able to comprise a transaction (e.g. transaction data) including one or more sender/seller identifiers, one or more receiver/buyer identifiers and metadata describing the parameters of the transaction (e.g. product description, price, time and/or other transaction parameters as described herein). For other block types, the block type-specific data 508 is able to comprise different information such as transaction/transaction block identifiers for pending/completed dispute blocks, dispute resolution transaction parameter changes for completed dispute blocks, updated or new user identification data and/or PPI (e.g. health status data) for genesis blocks and/or PPI update blocks, and other types of data discussed herein.

In some embodiments, the transaction of the block specific data 508 is able to further comprises a transaction subject field that identifies the purpose of the transaction (e.g. one or more token definitions/identifiers to be transferred, one or more smart contracts to execute) and a transaction target field that identifies the target of the identified purpose (e.g. an identifier of the MIDC/owner to receive a transfer of the subject token definitions/identifiers from the transaction originator; an identifier of the MIDC/owner for whom the subject smart contract is to be executed). Indeed, the inclusion of these fields within the data 508 allows for stronger control and security regarding cross-user interactions than is currently possible on existing smart-contract-capable blockchains, a feature that is advantageous in an enterprise environment. Similarly, the transaction headers provide strong definitions for determining whether a given transaction is merely an audit, and interaction between the system and a user (account recovery for example) or an interaction between two users (product purchase in a marketplace application).

FIGS. 8A and 8B illustrate an exemplary transaction 800 (of the block specific data 508) that are able to be used in the MIDC 202 or notary 206' chains respectively, according to some embodiments. As shown in FIG. 8A, the transaction 800 for a MIDC 202 is able to comprise a header 802, a payload 804, a signature 806 and a hash 808. The header 802 is able to comprise a transaction subject and transaction target data (as described above), a transaction type (e.g. PPI, dispute, or other types), a subject type 810, a subject other MIDC owner data (e.g. an identifier of a party to the transaction other than the MIDC owner if any), public key data (e.g. the public key of the owner of the MIDC 202), notary public key data (e.g. the public key used by the notary chain 206') and/or transaction generation time data. The subject type 810 is able to identify itself, the notary blockchain 206' or another MIDC 202. The payload 804 comprises the transaction details (e.g. PPI data, price data, and/or other transaction data as described herein). The signature 806 is able to comprise one or both of the digital signature of the local MIDC key signer (e.g. produced using the user's private key) and the notary signature (e.g. produced using the notary private key and used for certain transactions that are required to be signed by a notary key in addition to the MIDC key). The hash 808 is able to comprise a hash of the transaction. Similarly, as shown in FIG. 8b, the transaction 800 for the notary chain 206' is able to comprise a header 802, a payload 804, a signature 806 and a hash 808. The header 802 is able to comprise a transaction subject and transaction target data (as described above), a transaction type, a subject type 810, a subject MIDC owner data (e.g. an identifier of the MIDC owner), an identifier of the originator of the transaction (e.g. buyer), an identifier of the MIDC 202 of the originator, public key data (e.g. the public key of the owner of the MIDC 202) and/or transaction generation time data. The subject type 810 is able to identify the notary blockchain 206' or MIDC 202. The payload 804 comprises the transaction details (as described herein). The signature 806 is able to comprise the signature/signature string and the hash 808 is able to comprise a hash of the transaction.

Accordingly, by including only a single transaction and/or transaction header fields of the transaction subject and transaction target, the structure of the blocks 500 and the transaction stored on the blocks 500 provides the benefit of improved smart contract support, searchability, and integration with existing enterprise systems and applications.

The operating system 206 is able to include one or more user applications that enable the hardware of the operating system 206 (and/or the devices 104, 106) to perform one or more of the functions of the system 100 described herein. In some embodiments, the operating system 206 implements the application as a transaction website that using the devices 104, 106 the users are able to visit (e.g. via a web browser) in order to access the functions. Alternatively or in addition, the application is able to be downloaded onto and stored in the memory of the devices 104, 106 in order to provide the functions on the devices 104, 106 access the features (e.g. modules) of the operating system 206 described below. Specifically, the website and/or downloadable application are able to provide a graphical user interface for receiving and responding to commands/request/input from users and communicating that data to the operating system 206 via the networks 108. In some embodiments, as described in detail below, the application is able to be a transaction application that facilitates purchase and other types a transactions. In some embodiments, as also described in detail below, the application is able to be a health status monitoring application that facilitates the determination, monitoring and display of health statuses.

It is understood that although for the sake of brevity the discussion herein describes an exemplary distribution of performance the functions of the system 100 between the operating system 206 as operating on the servers (and/or in the form of a website) and/or the application as downloaded onto the devices 104, 106, it is understood that other function distributions between the application and operating system are contemplated including omission of the application such that the operating system performs all functions (e.g. with user interface functions being provided via a website).

The MIDC arrays 204, also referred to as a Chain Arrayed Data Store, are able to comprise one or more stacked MIDCs 202 such that the blocks of the MIDCs 202 are each a cell of the array with each MIDC 202 being a row of the array and the aligned cells of different rows forming the columns of the array 204. Each MIDC 202 (and thus each row) of the array 204 is dedicated to personal information about a single user/account, wherein any additional information or changes in information being reflected in additional blocks appended to the end of the MIDC 202 for that user/account. Accordingly, each MIDC 202 only ever represents one user and is the blockchain equivalent of all their data on a database. In some embodiments, each MIDC 202 comprises identification data (e.g. name) and personal data (PPI) (e.g. username/password, security questions/answers, age, image, voice, gender, medical statuses and/or other data associated with the user/account) associated with each other in their native format, a unique identifier assigned to the user/account/seller/buyer by the system 100 (e.g. alpha-numeric string), and de-identified data (e.g. an encrypted form of the unique identifier, identification data and/or the PPI).

As described in detail below, when a user registers with the system 100 (e.g. through the API gateway via a website, application, or other front-end user interface), their native identification and PPI and other data such as biometric data are captured, a new MIDC is created for this new user/account and a unique identifier is assigned to the user/account. This native identification and PPI data or other user data such a biometrics is then placed in a read-restricted "genesis" block on their MIDC 202. The PPI data and the unique identifier are then able to be encrypted by the system forming "de-identified" PPI. The de-identified PPI is then able to be placed in a new block on the MIDC 202 (appended to the genesis block) that is able to be read by the operating system 206 for use by the notary chain 206'. In some embodiments, any subsequent updates to the user identification and/or PPI are able to be incorporated with the existing data and incorporated into a new block on their MIDC 202 (and a subsequent de-identified version). In some embodiments, the previous, now outdated, genesis blocks become inaccessible (e.g. read restricted) as their data is now inaccurate. At no point is the notary chain 206 able to access the genesis block including the user PPI in its native form and thus the native form of this data is never posted or otherwise added to any of the transactions recorded on the notary blockchain 206'.

The new MIDC 202 is able to be stacked with any pre-existing MIDCs 202 (of other users/accounts) in order to form the MIDC array 204, which is able to fully emulate the functionality of an off-chain server-based database, without their inherent security vulnerabilities. As described above, any new or updates to the PPI of the user/account are added as a new block (that is not readable by the notary chain 206') on the user's MIDC 202 and then this new/updated PPI is encrypted with the unique identifier to create another "de-identified" block that is added to the end of the MIDC 202 of that user/account as a new block reflecting the new data/changes (and being readable by the notary chain 206'). In this manner the notary chain 206' is only ever able to access/read the latest block in a user's MIDC 202 which will only contain de-identified data enabling the GDPR, as well as global data privacy law compliance and security described herein.

The notary blockchain 206' is able to be a node cluster of a plurality of processing nodes (e.g. servers, computing devices, or other computing elements) implementing a proof of transaction consensus protocol (as described below) and a partitioned RAFT (P-RAFT) replication protocol, which is able to be implemented by the notary module as operating on each of the nodes, on a system server separate from the nodes, or both. Specifically, each node within the cluster is able to be a P-RAFT leader for a logical horizontal partition of the blockchain 206' and push/replicate its log (e.g. blockchain ledger of transactions) for that logical partition to a set number of the other nodes. Accordingly, each node is sent objects (e.g. pending/completed transaction objects, PPI objects, pending/completed dispute objects) for its given partition for which they are the only P-RAFT leader. The objects are able to originate from user devices 102, 104, servers 206 and/or other elements within the system 100. As a result, each of the nodes of the cluster are able to be both P-RAFT leaders of their partition as well as P-RAFT followers for other partitions.

When the node cluster boots up, all nodes participate in voting to determine an "orchestrator" node. The notary module of this orchestrator node then assigns each of the nodes to one or more of the partitions. Once determined, the partitioning schema indicating the partitions assignments of each of the nodes is replicated across every node in the cluster so that if the orchestrator node goes offline the partitioning schema is maintained and a new orchestrator node is elected. This orchestrator is able to reassign nodes to different sets of partitions as necessary to rebalance the partitions. A node may be assigned to one or more partitions by the orchestrator node. The precise number of partitions to which a node is assigned is configurable (this is the replication factor). Nodes assigned to the same partition elect a leader node for that partition. Alternatively, the notary module of the orchestrator node selects a leader for each partition based on a rotating scheme. The number of nodes in each partition is able to be dynamically adjusted by the orchestrator node.

There can only be one leader for any partitions. In the single fill partition mode, all other nodes are followers to the single leader. In the multi-fill mode, for each of a plurality of partition/leader node pairs, all other nodes are followers. A node may simultaneously be a leader for a particular partition and a follower in another partition in multi-fill mode. Nodes are able to only lead one partition at a time (but each node are able to be a follower for more than one partition). Leader and follower functions remain intact across single and multi-fill iterations modes. Leaders are changed based on a system algorithm like in RAFT. If a leader goes "offline" a new leader is automatically substituted, as if there was a "normal" leader rotation and like in RAFT, the consensus continues. Objects/transactions for that partition are not sent to any other node, and objects are delivered to the partition leader at least once.

As the objects are received (e.g. from user devices 104, 106, from other system elements described herein) at a central receiving server, they are able to be stored/buffered in a memory pool or buffer of the central receiving server. In some embodiments, the buffer is a first in first out (FIFO) buffer. Alternatively, one or more of the objects are able to be prioritized for assignment over other objects. For example, objects relating to pending and completed transactions (e.g. between a buyer and a seller) are able to be prioritized over pending and completed dispute objects and/or PPI objects, or vice versa.

Subsequently, the notary module is able to assign each of the buffered objects to one of the partitions and distribute that object to the leader node of that partition for recording on the designated partition as a block. In some embodiments, the notary module assigns sequential objects to the same one partition until such time as that partition is full, and then the next empty partition is filled until complete and so on. Alternatively, the notary is able to assign the objects to multiple different partitions in parallel, filling the partitions simultaneously and at possibly different rates. In such embodiments, an object partition distribution metric is able to be used by the module to assign received objects to one of the partitions. In some embodiments, the central receiving server is one or more of the nodes of the blockchain 206' (and/or MIDC 202). Alternatively, the central receiving server is able to be one or more of the servers storing the platform operating system 206.

For example, in some embodiments the assigned partition is determined by finding the modulus of a hash of an identifier (e.g. assigned partition=hash(object identifier) % number of available partitions) of the object (e.g. the public key, private key, object/transaction identifier, other data of the object/transaction as described herein, and/or a combination thereof such as a concatenation of two or more of the values). Alternatively or in combination, other object partition distribution/assignment methods are able to be used such as assigning objects based on a fullness level of each of the partitions (e.g. assigning to the least full) and/or a number of pending objects that are waiting to be added to the partitions (e.g. refraining from assigning to a partition if a number of pending objects meets a threshold level). In some embodiments, if an object references a specific prior block/object (e.g. a completed transaction object referencing a previously recorded pending transaction object), the object is able to be routed to the leader node for the partition storing that block/object even if applying the distribution metric to the object would have assigned a different partition for the object.

In response to receiving an object assigned to a partition that they lead, the nodes store the object locally and push/replicate it to a configurable number of the other "follower" nodes in the cluster (e.g. all or a subset of the other nodes). Upon receiving confirmation that the object is verified (e.g. when the node has determined that the objects are not poisoned and/or that the objects are valid based on the proof of transaction consensus described herein), the nodes add the object as a block to the assigned partition locally and broadcast a confirmation to those follower nodes indicating for them to also add the objects as a block to their copy of the assigned partition locally. Thus, each node receives, shares, confirms and records objects (e.g. signed transactions) as blocks for partitions for which they are a leader, while concurrently receiving shared objects, receiving object confirmations, and locally recording confirmed objects on partitions for which they are a follower. In some embodiments, each of the nodes maintain the persistence layer (e.g. direct to attached disk volume) for "their copy" of the partitions they both lead and follow. In some embodiments, each of the leader and/or follower nodes process each received object in an idempotent manner.

The size and scope of the partitions are able to be determined by the notary module autonomously. For example, the blockchain 206' (e.g. the memory of the nodes storing the blockchain) is able to be pre-sharded in equal sized logical partitions by default. Alternatively or in addition, the size and scope of the logical partitions are able to be dynamically adjusted and/or manually input by a user. In some embodiments, the notary module is able to dynamically adjust the size and/or quantity of the partitions based on the load of each partition (and the associated nodes) to prevent transactional and computational overload. However, because the system can be dynamically horizontally scaled by adding computing resources, dynamic addition of computing resources is the preferred methodology to adjust for spike in object processing needs, As a result, this partitioned P-RAFT notary and replication provided the benefit of distributing the notary and replication workload thereby increasing object speed while still providing object security. Although described above with respect to the notary blockchain 206' for the sake of brevity, the above features are able to equally apply to the MIDCs 202 implemented by the notary module and/or other modules of the operating system.

Figure 6:
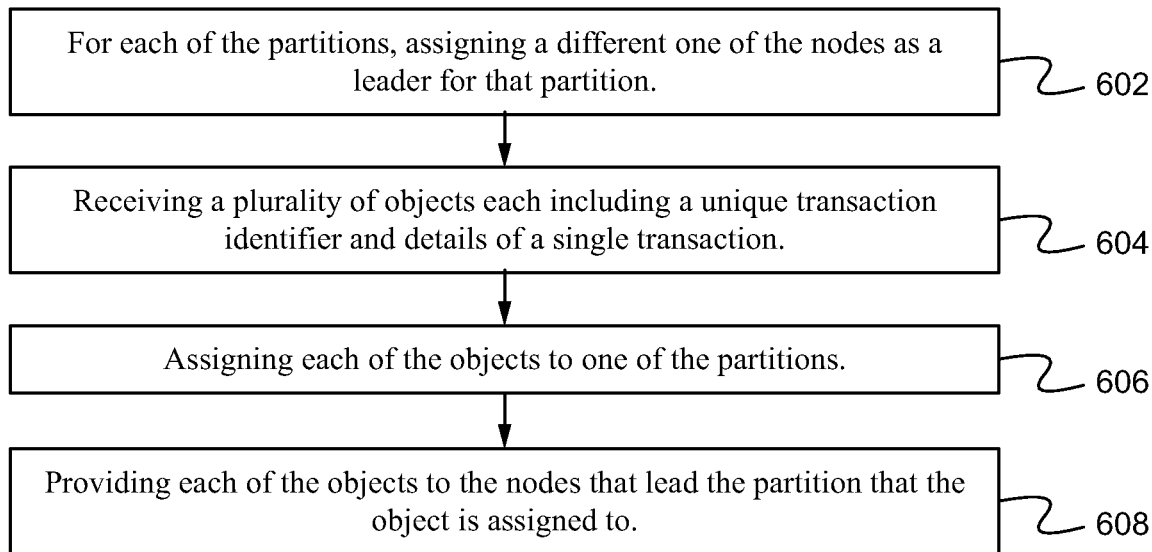
FIG. 6 illustrates a method of replicating objects on a blockchain according to some embodiments.

FIG. 6 illustrates a partitioned RAFT method of replicating object/transactions on a blockchain 206', 202 according to some embodiments. As shown in FIG. 6, for each of the partitions, the platform operating system (as executed by the platform server(s)) 206 assigns a different one of the nodes as a leader for that partition at the step 602. The platform operating system 206 receives a plurality of objects each including a unique transaction identifier and details of a single transaction between any two or more of the users at the step 604. The platform operating system 206 assigns each of the objects to one of the partitions at the step 606. The platform operating system 206 provides each of the objects to the nodes that lead the partition that the object is assigned to at the step 608.

In some embodiments, the method further comprises each node of the nodes receiving a number of the objects (e.g. from the operating system 206 and/or other nodes), and for each of the number, determining whether the object is assigned to the partition that the node is the leader of or a follower of. If the node is the leader of the partition, the node stores the object and sends copies of the object to the followers of that partition. Subsequently, upon receiving confirmation in a verification message (e.g. from the operating system 206) that the object is authentic (e.g. consensus successful for the object, no poisoning found in the object, object properly formatted), the node locally posts the transaction object as a new block on the notary and/or MIDC blockchain on the partition that the node leads and distributes a confirmation message to the followers of the partition that indicates that the object is valid. In contrast, if no verification message is received after a predetermined period and/or the verification message indicates that the object is not authenticated (e.g. consensus unsuccessful for the object, poisoning found in the object, object improperly formatted), the node locally deletes the transaction object and distributes a confirmation message to the followers of the partition that indicates that the object is invalid. Alternatively, the node is able to omit sending a confirmation message to the followers if either no verification message is received after a predetermined period and/or the verification message indicates that the object is not authenticated and the follower nodes automatically delete the object locally after not receiving a confirmation message within a predetermined period.

If the node is a follower of the partition, in response to receiving a node confirmation message from another of the nodes indicating that the object is valid, locally posting the object as a block on the notary and/or MIDC blockchain on the partition to which the object is assigned. Additionally, as described above, if the node is a follower of the partition, in response to not receiving a node confirmation message for the object within a predefined period or receiving a node confirmation message indicating that the object is not authenticated, locally deleting the object. In some embodiments, the method further comprises the operating system 206 dynamically adjusting a size of one or more of the partitions from an initial size to a different size. In some embodiments, the method further comprises the operating system 206 storing the objects in the transaction buffer before assigning them to a partition and sending them to one of the nodes.

In some embodiments, the assigning each of the objects to the one of the partitions comprises determining a hash M of the transaction identifier of the object and determining M mod N, where N is the number of leader nodes. In some embodiments, the assigning each of the objects to one of the partitions is based on congestion levels of each of the nodes that are one of the leaders. In some embodiments, the assigning each of the objects to one of the partitions comprises disregarding results of the assignment metric if the object points to an existing block on the blockchain and assigning the object to the partition in which that block is stored. In some embodiments, for each of the objects provided to a leader node, the operating system provides a subsequent verification message to the leader node indicating that the object provided is authenticated or not as described above.

Operating System

The operating system 206 is able to comprise a registration module, a key module, a notary module, a biometric module, an authentication module ("Rosetta"), a block loader module, a privacy law and regulatory law compliance module, a sales module, a purchase module, an anti-poisoning module, a payment processing module, a ledger module, a hardware security module, attack defense module, a DeHI module, a token ecosystem module, an international token exchange module, a medical status module and/or a dispute module. Alternatively, more or less modules (and/or micro-services) are able to be used and/or one or more of the modules and/or micro-services (and their associated functions) are able to be combined or divided. Module is interchangeable with "micro-service" herein. These modules are able to be implemented by the operating system 206 as it operates on the blockchain cluster of nodes, as a website provided by one or more servers/nodes, and/or by an application downloaded onto the devices 104, 106.

Registration Module

The registration module enables a user (i.e. buyer/seller) to create an account on the transaction system 100 by inputting private personal information (PPI) such username and password information, a native identifier (e.g. name), personal information about the user, contact information (e.g. phone number, email), privacy regulation compliance metadata (e.g. age, current location, privacy preferences) and/or banking information via a graphical user interface (e.g. of a website and/or transaction application). In some embodiments, the personal information includes biometric data (iris scan, voice recording, fingerprint scan, facial scan, blood type, other biological characteristics or any combination of the foregoing) for implementing biometric verification. In some embodiments, this biometric data is also used to enable access to the platform, or for access to transactionality or protected function on the platform. For example, the platform is able to implement a biometric login and registration and subsequent access restriction as described in U.S. patent application Ser. No. 17/025,924, filed Sep. 18, 2020, and entitled "DYNAMIC BIOMETRIC IDENTITY VERIFICATION SYSTEM, METHOD AND DEVICE," which is hereby incorporated by reference. Alternatively, the biometric login and registration and access use is able to be omitted and/or other biometric access methods are able to be used.

In some embodiments, the personal information is able to be omitted for a user that is a seller. This account information is then associated with a newly generated account and stored on a new MIDC 202 for the user along with a platform-generated unique identifier (as described above) such that the information is able to be used to identify the user when logging onto the platform 102 and other functions of the platform 102. The personal information is able to comprise one or more of the account owner's age, gender, address, income level, religion, political affiliation, race, nationality, interests, height, hair color, eye color, weight, medical conditions, family members, education level, degrees earned, occupation, passport number, driver's license number, IP address, device identifier, work address, work phone number, banking account number, social security number, date of birth and/or other characteristics of the user. After the account is created, the user is able to access the account and any associated data (e.g. to edit the personal data) by entering the username and biometric data and/or a password in order to identify themselves to the system 100.

Figure 7:
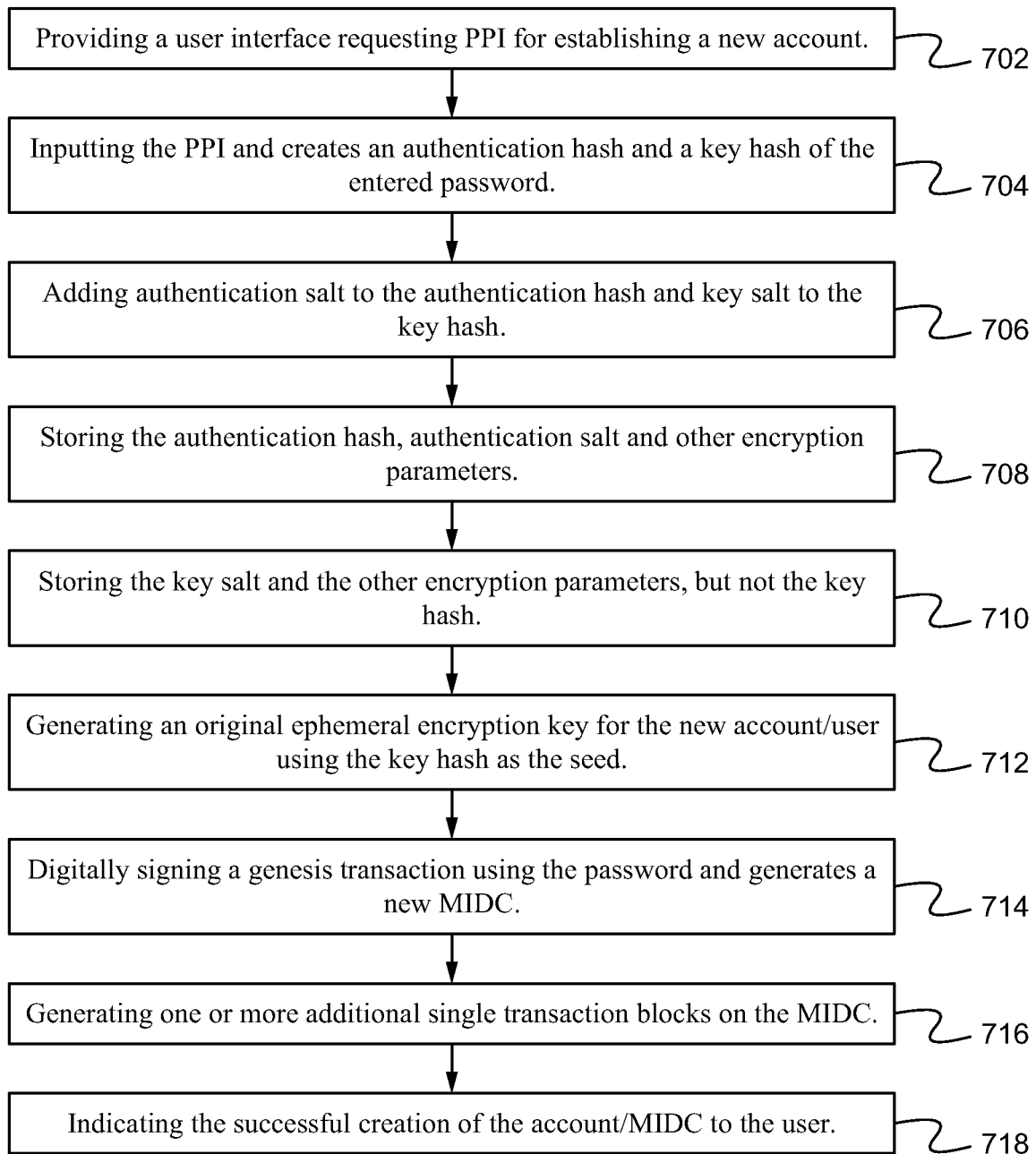
FIG. 7 illustrates a user registration method according to some embodiments.

FIG. 7 illustrates a user registration method according to some embodiments. As shown in FIG. 7, the registration module provides a user interface requesting PPI for establishing a new account at the step 702. The PPI requested is able to include identification information (e.g. name, username), password information, personal information about the user, contact information (e.g. phone number, email) and/or banking information. The registration module inputs the PPI and creates an authentication hash and a key hash of the entered password at the step 704. The registration module is then able to add authentication salt to the authentication hash and key salt to the key hash at the step 706. The registration module stores (e.g. in the vault) the authentication hash, authentication salt and other encryption parameters at the step 708. The registration module stores the key salt and the other encryption parameters (e.g. in the vault), but not the key hash at the step 710. The registration module generates an original ephemeral encryption (EC) key for the new account/user using the key hash as the seed at the step 712. The registration module digitally signs a genesis transaction using the password and generates a new MIDC 202 with the first single transaction block being the genesis transaction at the step 714. This MIDC 202 is then able to store transaction associated with the user and thus be the user's personal MIDC 202. In some embodiments, a message indicating the creation of this new MIDC 202 is able to be transmitted to the notary module, which is able to record a transaction identifying the creation of the new MIDC (using an alias to identify the user/account such as an alphanumeric string).

After creation of the genesis block, the registration module generates one or more additional single transaction blocks on the MIDC 202 at the step 716. These additional blocks are able to include a PPI transaction including the PPI submitted by the user, a password recovery transaction including password recovery information (e.g. security question data) and/or a biometric data transaction including biometric data of the user (e.g. inputted using a biometric login/registration as described above). The registration module is then able to indicate the successful creation of the account/MIDC to the user via the graphical user interface at the step 718. In some embodiments, upon completion of the registration the registration module is able to generate (and/or request/input from a vault described below) a JSON web token (JWT), sign the JWT with the user's ephemeral EC (private) key, and transmit the signed JWT to the user device to authorize the user device's session on the platform.

After the registration process has been completed, a user/device is able to subsequently log into the platform 102 by submitting their password as a part of a login request. In response, the registration module submits an authentication verification request with the password to the key module, which retrieves the password salt, encryption parameters and authentication hash for the user. The key module is then able to use the parameters (e.g. argon2id parameters) and salt to recalculate the authentication hash based on the submitted password and compare the produced value to the stored hash value for that user/account (determined during the registration process). If the values do not match, the registration module issues a failure message to the user. If the values do match, the registration module signs, issues a JWT, and transmits the token to the user/user device which the device is able to use to access the platform 102. In some embodiments, the registration module is implemented by an application program interface (API) gateway within the platform 102.

Key Management

The key module enables generating and storing of keys and other types of secrets (e.g. unique identifiers) for use with the platform 102. Once a user has entered their PPI and created an account on the platform 102, the key module generates a unique identifier for that user/account (e.g. alpha-numeric identifier) and user/MIDC keys and/or ephemeral keys for that user/account/MIDC that are used to sign transactions, encrypt/view data on the MIDC 202 and sign on to the platform 102. Subsequently, the module encrypts both the unique identifier and the PPI associated with the account and stores it on a block added to the genesis block of the MIDC 202 for that user. As described above, unlike the protected genesis block (including the native PPI and unique identifier) this added block (e.g. the latest block) of the MIDC 202 is able to be accessed by the notary blockchain 206' and/or notary module of the operating system 206 in order to sign/record transactions on the platform 102. In some embodiments, the key module utilizes user passwords (e.g. inputted during registration) with/or without biometric data in order to derive the encryption and signing keys for the user's MIDC 202 and PPI. In some embodiments, the passwords are hashed using the argon2 ID algorithm. For example, in some embodiments the user keys for the MIDCs 202 are deterministically and ephemerally generated by the key module when needed based on both a cryptographically secure hash of the user's password and a secret cryptographic salt. The parameters necessary to derive the MIDC key pair are able to be stored in an MIDC vault that is able to be separate from or a part of the arrays 204. This MIDC key is only used to sign MIDC transactions on behalf of the user and is not compatible with the notary blockchain 206'. In some embodiments, the key module inserts a secret identifier (e.g. zero-watermark) into the MIDC key pairs. As a result, the key module is able to look for the secret identifier in any a public/private key that a device/user is attempting to use and determine if the key is fraudulent if it does not contain the secret identifier.

The MIDC keys are able to be used by the buyers/sellers and/or the notary blockchain 206' to log onto the platform 102 as well as to digitally sign transactions/smart contracts in order to effectuate the transactions on the platform 102. In other words, the public key of this pair (the user's "Pubkey") is the user's primary visible identifier within the platform 102, and is also used to encrypt data that only they should be able to read. The private key of the pair is used to sign their MIDC transactions (most user operations) and to sign their JWT to begin authenticated web sessions. Further as described above, in some embodiments the user private keys are not persistently stored by the platform 102. Instead, they are ephemeral and/or regenerated each time they are required using the user's password (and salt and/or other derivation factors). In some embodiments, user keys use Elliptic Curve P256-NIST cryptography.

Like for the user MIDCs 202, the key module is also able to generate notary key pairs for use by the notary blockchain 206 and/or the notary module of the operating system 206 in order to sign transactions and perform other functions. The notary keys are generated and stored in a vault implemented by a MIDC array 204 (e.g. MIDC vault) that the notary chain 206 must query when the keys are needed for signing transactions or other functions. The notary blockchain keys are able to be generated within the MIDC vault by the key module and may not be exported. The notary module is the only module within the cluster permitted to execute operations with these keys (e.g. sign, encrypt, decrypt, etc.). As a result, the notary private keys are never known or accessible by the system. In some embodiments, the vault is operated by a hardware security module (HSM) operating a vault gateway. Alternatively, the vault and vault gateway are able to be operated without an HSM.

In some embodiments, if the notary module needs to sign transactions that go onto the MIDCs 202 (e.g. records of transactions that have been committed to the notary blockchain 206' and need to also be reflected on the seller/buyer MIDCs 202), the key module is able to issue one-time-use keys for the primary MIDC signature and also require an additional signature with the notary key to ensure the transactions are validated by the notary module itself. In some embodiments, the MIDCs utilize 256-bit EC keys and the notary uses 384-bit keys. Alternatively, other key sizes are able to be used. In some embodiments, the notary keys are intentionally made to be inoperable with the MIDC keys (e.g. using a P384 elliptic curve) thereby providing an added layer of security.

In some embodiments, during login and registration establishing initial PPI and/or any time a user wishes to add new PPI, a copy of data needed for account recovery is added to their MIDC 202 using a key deterministically derived from an enrolled recovery method (e.g. a hash of a known private secret combined with an un-stored user identifier generated during voice biometric enrollment). When a user wants to recover their account or reset their password, the biometric module (sometimes referred to as the biometric lock) and/or other alternate identification method (e.g. security questions, two-way verification, or other methods), re-identifies the user (e.g. using voice and/or facial identification methods with/or without proof of liveness AI assisted questions that work with the users biometrics) and returns the same identifier used when the user first enrolled (e.g. voice data, facial image data, security question data and/or other data). The original key pair is then re-calculated and used to execute an account recovery smart contract on the original MIDC 202 of that user, migrating the data from that MIDC 202 to a new MIDC 202 with a genesis block created by the user's new password.

In some embodiments, the platform 102 is able to comprise multiple parallel operating instances. In such embodiments, within an instance, a user's/account's public key is representative of their identity because it also represents their entire MIDC 202 including the stored PPI, account recovery data (e.g. smart contract) as well as MIDC vault storage of related secrets, authentication data and compliance metadata. Within a platform instance that supports multiple notary modules and/or notary blockchains (e.g. instances that share MIDC arrays), the same applies. However, for isolated instances with separate dedicated notary blockchains/modules and MIDC arrays 204, the MIDC vault key derivation parameters are able to be shared between instances allowing the user/account to authenticate using the same credentials (e.g. password) on any of the instances while the PPI of the user/account would still be specific to each instance. To keep the MIDC vaults isolated, in some embodiments credentials and keys would be entirely separate (e.g. such that the user/account could have different passwords on one instance verses another). If biometric-based account recovery is used, that user/account is able to recover their account on any instance regardless of which data is on which instance.

As mentioned above, PPI is encrypted using the user's own private key, which is ephemeral. However, if the private key required to decrypt this data is not available to the system, then system administrators cannot securely access user information where permitted by law. As a result, in some embodiments under the default configuration (and depending on the precise secret), when a user adds secret information/PPI, an additional copy of the information/PPI is created and encrypted for administrative purposes (e.g. using an Elliptic Curve P512 key). The private key to decrypt this information/PPI copy, though not ephemeral in the same way as the user's private key, is not stored in the system in plain text but instead is able to be double or triple encrypted using each admin's unique ephemeral private key and either or both of another admin's or Rosetta's system key. In this way, admins can access the certain user information/PPI and other secrets while maintaining the full system strength afforded by the ephemeral key architecture.

Attack Defense

In some embodiments, the platform 102 is able to include an attack defense module. For example, in order to increase the number of users within the platform to the level of hundreds of thousands, the attack defense module is able to implement a custom Log-structured Merge Tree (LSM tree) modeled to represent the platform's blockchain structure as directly as possible for efficient disk interaction across the spectrum of data operations. In some embodiments, the attack defense module is able to implement fast secure anonymized searching (for example, an administrator is able to quickly search for a user or user account without the need for any read operation on that user's secure data to take place). In some embodiments, at the application layer, the attack defense module includes additional software libraries and tools for application developers to reduce or eliminate the possibility of introducing cross site scripting (XSS) attack and injection vulnerabilities, explore state-of-the-art techniques in steganography, biometric access, edge computing, and stream-based encryption to combat phishing, and improve machine learning models to detect anomalies in user behavior to identify and stop malicious actors. In some embodiments, the additional security protocols are at the operating system 206 and the hardware levels.

In some embodiments, in order to further harden against attacks originating from privileged OS users, the attack defense module uses a watchdog process to ensure that the main platform process itself is not tampered with and to monitor for suspicious activity on the host machine. In the event of a suspected attack in progress, the watchdog protocol is able to cut all active shell connections. If the connection between the watchdog and platform is severed, the attack defense module is able to have the affected node removed from the network.

In some embodiments, the platform 102 comprises a custom kernel to allow the watchdog process to protect itself from attack by privileged users, and to provide protection against memory-sniffing and side-channel attacks by adding a degree of randomization to speculative execution attacks that use algorithms to obtain sensitive data where the attack relies on tracking the execution time of mis-speculated calls as their side-channel. By adding random delays to execution times (e.g. block recording processing actions) to this timing the side-channel is disrupted and the attack becomes impossible. In certain iterations this may be combined with whitelisting access to certain instructions like flushing the L1 cache.

In some embodiments, at the hardware level, the platform 102 reduces the amount of data being vulnerable to hardware-level attacks in the first place by employing homomorphic encryption. In some embodiments, the attack defense module is able to protect against hardware level attacks by adding hardware cryptography devices like HSMs for various cryptographic operations.

Secure Data Viewing

The authentication module ("Rosetta") enables users to encode/decode and/or read data on the MIDCs 202 in order to access information about their own data, their transactions and/or the other parties to the transactions (while it remains on the user's MIDC 202). Specifically, when it is needed, Rosetta acts as a "decoder" to temporarily allow an appropriate system approved user (subject to certain rules and permissions) to temporarily view that PPI for approved purposes (i.e., accounting, shipping, verification, etc.). The PPI is never moved off the user's MIDC 202. Rosetta allows it to always stay there. No personal data exists anywhere on Rosetta other than the MIDC 202 where it resides. As described herein, the notary blockchain 206' uses an encrypted, substituted and anonymized/pseudo anonymized identification data and unique identifiers for buyers and sellers. These identifiers on the notary blockchain 206' act as pointers for Rosetta to locate the relevant "Buyer" and/or "Seller" identifiers for a transaction, so Rosetta can allow an authorized user to see that PPI, after Rosetta locates and decodes it from the MIDC 202 of those identified/pointed to buyers/sellers. Additionally, Rosetta is able to authenticate and authorize user sessions for the platform 102, sign user transactions, tokenize data for PPI searches, create permissioned copies of PPI for parties authorized to access it by users during the course of transaction execution, re-encrypted with the receiving party's key, set up and manage stenographic pipelines for important flows like registration and login and/or other authentication functions.

Additionally, if a user wishes to view data stored on another user's MIDC 202 (e.g. from a previous transaction between the users), Rosetta is able to securely provide access to view that data (assuming the user has authority to view that data). For example, if a first user 23 (that has been authenticated) issues a request to Rosetta to view data (e.g. a specified transaction) of a second user 25, Rosetta parses the request for the user 23 password and the target MIDC, user and/or transaction identified in the request. Rosetta is then able to generate a certificate (e.g. public key infrastructure key) using the user 23 password and/or other data (e.g. user password, salt, other parameters and/or hashes thereof) and send the certificate to the key module in a request for the key derivation parameters for user 23 stored on the platform 102 (e.g. on the MIDC vault controlled by the key module or elsewhere on the platform 102). If the certificate is authentic (e.g. the password and other parameters used to generate the certificate were correct), the key module retrieves and transmits the user 23 key derivation parameters to Rosetta which is able to user the received key derivation parameters (e.g. along with the user password and salt) with a key derivation function (e.g. Argon2) to derive a key seed. Rosetta is then able to use the key seed to dynamically generate the user 23's key pair using the same key generation function that was used by the key module to originally generate user 23's key pair (e.g. EC256).

Further, Rosetta is able to retrieve the MIDC block of user 25's MIDC 202 including the data that user 23 is permitted to view (e.g. the transaction including user and/or identified within the initial request). In particular, the target block of user 25's MIDC (or a copy thereof) is able to be encrypted using the public key of user 23, securely transmitted/presented to user 23, and then decrypted by Rosetta using user 23's dynamically regenerated private key. Accordingly, Rosetta is then able to present the data to user 23 (e.g. in memory only through secure data channel) for view via the graphical user interface of the platform 102 (e.g. application, browser/website, and/or other graphical user interfaces). In some embodiments, even after decryption the data is scrambled such that Rosetta further needs to descramble the text using a descrambling algorithm before it is presented to user 23. Therefore, Rosetta provides the advantage of enabling authenticated users to view data on other user's MIDCs 202 while still maintaining data security.

Figure 9:
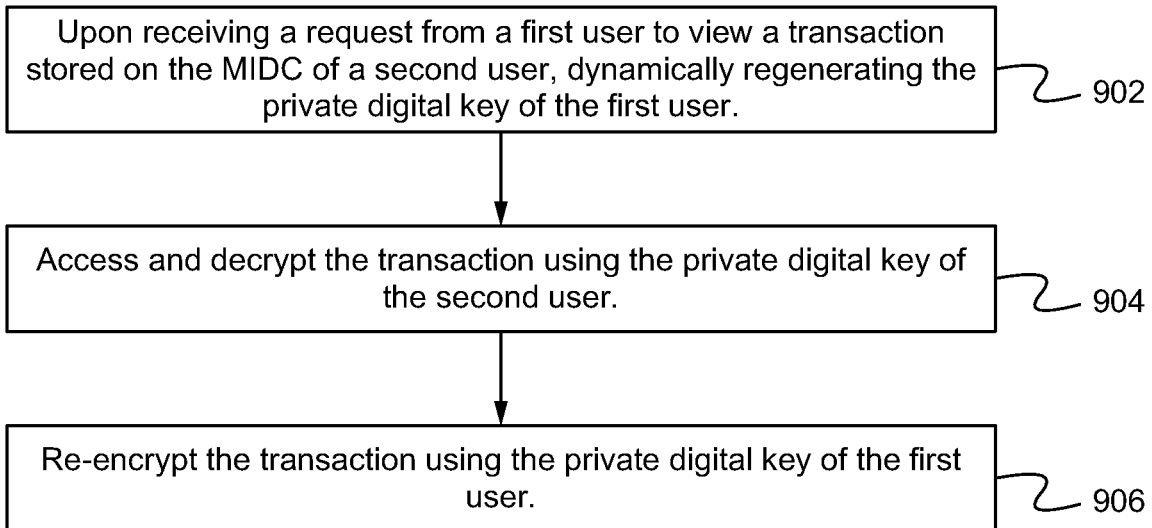
FIG. 9 illustrates a method of securely providing MIDC data to a user according to some embodiments.

FIG. 9 illustrates a method of securely providing MIDC data to a user according to some embodiments. As shown in FIG. 9, upon receiving a request from a first user to view a transaction stored on the MIDC 202 of a second user, Rosetta dynamically regenerates the private digital key of the first user at the step 902. Rosetta accesses and decrypts the transaction using the private digital key of the second user at the step 904. Rosetta re-encrypts the transaction using the private digital key of the first user at the step 906.

Database Importing

The block loader module enables a user to load an existing database into the MIDC array 204 to simplify, and automate, user migration from a DBMS to the transaction platform 102. Since the MIDCs 202 of the platform 102 use single transaction blocks for each transaction and/or dataset, each block of an MIDC 202 is the functional equivalent to a "cell" in a database such that the entire chain of the MIDC 202 is the functional equivalent to a separate row in the database and the blocks that align between the MIDCs 202 when they are stacked on top of each other (in the array 204) are the functional equivalent to a separate column in the database. Thus, the stack of MIDCs 202 of separate users forming the MIDC array 204 of the platform 102 is able to form a functional equivalent of a database with columns and rows.

Because of this MIDC array 204 structure (e.g. stacked MIDCs each dedicated to a separate user), the MIDC array 204 is searchable and has create, read, update and delete functionality like a database. The delete functionality is achieved by deleting the entire MIDC 202 like deleting an entire row of a database (and replacing it with a new MIDC 202 if desired such as for user password/account reset). Append is able to be achieved by creating additional single transaction blocks for the associated chain 202 with additional data reflecting the new/updated data (wherein the authentication module Rosetta is structured to look for the block in an MIDC with the "latest" data whether it is a block containing a revised address or other PPI for a user, or a block in a series of blocks for a particular transaction that might show a shipping change or dispute resolution for example).

As a result of the MIDC array 204 structure, the block loader module is able to migrate the cells, rows and columns of databases to the functional equivalent blocks, chains and aligned blocks in stacks of chains of the MIDC array 204. Thus, the block loader module is able to effectuate a migration of an existing database to the platform 102 while preserving the structure and data of the original database it was on. In some embodiments, the block loader is able to automate this migration and utilize a cloud-based structure to achieve this migration.

Privacy Law and Regulatory Law Compliance

The privacy compliance module automates and maintains data privacy law and regulatory law compliance functions, so that data on the system—from original collection, through storage, curation, retention and deletion—is done in such a way that the data is always in compliance with all global data privacy laws and regulatory laws (e.g. health insurance portability and accountability act (HIPAA), financial industry regulatory authority (FINRA), securities and exchange commission (SEC), know your customer (KYC), anti-money laundering (AML), etc.). First, all global data privacy laws and regulatory laws, be they county, state/provincial or category specific (e.g. general data protection regulation (GDPR), California consumer privacy act (CCPA), federal information security modernization act (FISMA), health insurance portability and accountability act (HIPAA), payment card industry (PCI)) are broken down and loaded as rules into the privacy compliance module engine and/or stored in a compliance memory of the system 100. Second, each time user data (e.g. PPI) is added to the platform 102, the module uses geolocation functions (e.g. upon user registration and/or log on to the system) to determine their location and access the associated stored privacy rules based on the determined location. Third, the module applies the identified rules to the data. In some embodiments, the rules are automatically periodically updated and adjusted to changes in the law such that they always apply the most up to date rules to each set of data on the platform 102. In some embodiments, the privacy compliance module uses AI/Machine Learning to assist in the application of the aforementioned rules, along with geo-locating all users, at all times to automate data privacy law compliance. In such embodiments, the compliance memory is able to also store a knowledge base for applying the loaded rules to the users using the AI/machine learning.

For example, if the platform 102 is deployed by a medical office in Los Angeles, CA and after January of 2020 the compliance module sees a user on-board to the platform 102, the privacy compliance module applies the appropriate data privacy law rules to that user's data (e.g. PPI) including; but not limited to: CCPA+HIPPA+PCI which are all applicable for that location. As another example, if the platform 102 is deployed for a hotel chain and the user originally on-boarded in London where the privacy law and regulatory law compliance module/engine applied GDPR+PCI and any other relevant and appropriate data privacy laws to the user's data for that location. That user then travels to Beijing and checks into a hotel chain's property there. Because the privacy law and regulatory law compliance module geo-locates the user for each and every transaction that they make on the platform 102, it will automatically determine the new location and additionally apply Chinese data protection and regulatory law and any other Chinese law governing the transfer of data to jurisdictions outside the territorial boundaries of China. As a result, the privacy law and regulatory law compliance module/engine provides the benefit of automating compliance with data privacy law and regulatory laws even when involving multiple jurisdictions and types of laws.

This functionality applies to users electing to enforce their Right of Erasure as well. While users have the unfettered right to erase their data, most times that erasure is not immediate. Global data privacy laws have exceptionalities of holdbacks that allow companies to not immediately erase a user's data even after they have enacted their Right to Erasure. A sample of reasons for such delaying of erasure include provision in global data laws for: credit care charge-back periods, to comply with tax laws, or for contract reasons, public interest, research, etc. all with different allowable tolling periods.

As a result, the privacy compliance module also enables a user/entity operating the platform 102 to select any of the erasure delaying provisions that apply to them and the module will then automatically implement those delays (e.g. start a timer or otherwise monitor when in the future the data should be erased and then effectuating the erasure at that time after the appropriate delay period has elapsed). In particular, when a user elects to exercise their right of erasure of their stored PPI, the privacy compliance module automatically:

1. Transmits a message to the user indicating that they system has time-stamped their erasure request.
2. Transmits a message to the user indicating any legal tolling/delays that apply to their requested right of erasure.
3. Sets a clock or other timing function, based on the user time-stamped deletion request, as to when deletion is to be made upon the expiration of said tolling period.
4. When that tolling period expires, effectuates the user's Right to Erasure request by deleting that users MIDC 202 and notifies the user that their data has been removed from the system.

Finally, in the unlikely event of a breach of the system (or any event resulting in disclosure of some or all of one or more user's PPI) the privacy compliance module will, taking into account the applicable data privacy law (based on the user(s) and their location), automate and effectuate the reporting of said breach to both users and the appropriate regulatory agency(s). Thus, the platform 102 provides the benefit of being autonomously, and in real-time, with zero-trust, being compliant with GDPR, CCPA and other all data privacy laws while maintaining the benefits of the block-chains immutability.

Transactions

The sales and transaction module/engine enables a user/seller to input product and/or service information (e.g. description, price, delivery options and other product/service details) that the seller wishes to provide for sale on the platform 102. In some embodiments, the sales module provides a unique identifier for each of the products/services. Upon submission of the product/service information, the sales module generates a smart contract that reflects the indicated parameters of the sale of the product/service along with the encrypted seller unique identifier and/or the product/service identifier. The sales module then adds this smart contract and the identifier(s) as a single transaction block for each product/service on the seller MIDC 202. In some embodiments, the sales module requires the seller to submit their password before generating the smart contract. In particular, the sales module is able to provide the submitted password to the key module, in the same manner as described below for a buyer transaction, in order to dynamically generate the private key of the seller (for encrypting the single transaction block including the smart contract). Alternatively, the product/service transaction blocks are able to be stored in a different location such as a different MIDC array 204 and/or other type of memory. Again, because the native user identifiers are not used, the information stored on these product/service blocks of the seller/buyer MIDCs 202 is fully de-identified (fully encrypted, pseudo anonymized and anonymized) such that it is not connectable to any natural user identification information.

The purchase module enables a user to view and purchase one or more of a list of products and/or services that have been provided for purchase by the sellers via a smart contract on a block on the seller's MIDC 202 on the platform 102. Specifically, the products and/or services presented are able to reflect the terms of the open smart contracts for the products and/or services created by the sellers and stored on the seller MIDC 202 such that the buyers are able to choose whether they agree to those terms and to complete the smart contract.

Once a buyer selects one or more products of a seller and submits a purchase command to the purchase module (e.g. via a buyer device 104), the purchase module checks the buyer and seller credentials by accessing the buyer's MIDC 202 and the seller's MIDC 202 to determine if they are in good standing, meaning they have been determined to not be a user that has engaged in fraudulent transactions or one that has been flagged and or removed from the system for malevolent behavior such as trying to either chain-poison the system or compromise the cybersecurity of the system. If the credentials for both the buyer and the seller are able to be verified/authenticated, the purchase module generates a pending transaction object for the buyer and the seller. In some embodiments, the purchase module requires the buyer to input their password before it will generate the pending transaction object. Alternatively or in addition, the purchase module is able to use the password of the buyer as submitted by the buyer when logging into the system.

In some embodiments, generating the pending transaction objects is able to comprise requesting the password authentication hash and/or the private key derivation parameters (e.g. as stored in the vault) from the key module. The key module determines if the purchase module's context permits reading of the authentication hash and/or key derivation parameters, and if so, retrieves them from the vault. With these values, the purchase module computes the authentication hash of the user/buyer password (e.g. submitted by the buyer as a part of the transaction and/or login) and compares with a stored authentication hash value (determined and stored during the registration of the user/buyer). If the values do not match the verification/authentication fails and the object/block is not created and/or discarded. If the values do match, the purchase module dynamically regenerates the private key of the user/buyer using the received key derivation parameters and signs the transaction request in order to form the buyer/user pending transaction object. In a similar manner, the purchase module is able to request, receive and generate the private key of the seller and then sign the transaction request in order to form the seller pending transaction object. After the purchase module has formed the buyer/user pending transaction objects the user password and regenerated private key are deleted from the system. In some embodiments, the purchase module decrypts PPI requested by the seller and re-encrypts the data using the seller's public key such that it can later be viewed by the seller (e.g. upon completion of the transaction using the authentication module). If the verification/authentication fails, the transaction request is rejected and the transaction is terminated.

The pending transaction object is able to comprise information about the transaction including, but not limited to, one or more of: the terms of the contract for the product (as input to the platform by the seller as described above), the buyer unique identifier, the seller unique identifier, the product(s) identifier(s), the date/time, a transaction hash, a generated transaction identifier, product(s) information and/ or other data about the transaction. The purchase module is able to determine the appropriate product contract information/terms using the product identifier included in the purchase request as a pointer to the product information and contract terms on the MIDC 202 where it was uploaded by the seller (as described above).

For each generated pending transaction object, the anti-poisoning module inputs the transaction and determines if it includes any illegal, malicious, cybersecurity compromising, ransomware, malware, phishing or pornographic content etc., (e.g. using image and text analysis engines; identifying if the object includes any extraneous data; identifying if the object has the correct format and/or comparing the data of the transaction object to a set of known illegal images, malware, ransomware, phishing and/or other data). If illegal content is found, the module is able to terminate the transaction object and/or remove the illegal content from the object or rejects the transaction in its entirely and removes the content and pending block by deleting it from the system. It is able to in some embodiments delete the user and their MIDC from the system altogether.

If the anti-poisoning module approves the pending transaction objects of the buyer and the seller, the purchase module posts the pending transactions objects to the buyer and seller MIDCs 202, respectively, signs the pending transaction object with both the buyer and seller private keys, and transmits the signed pending transaction object to the notary module/notary chain 206'. In some embodiments, the signing comprises sending confirmation requests to the seller/buyer devices 104, 106, wherein the confirmation requests comprise a challenge message that needs to be digitally signed by the buyer and seller devices 104, 106 using their respective buyer/seller encrypted keys (e.g. as dynamically generated by the key module upon request). These digital signatures are able to later be validated by notary module (e.g. using the associated paired keys known by the key module) as a part of determining if there is consensus for the transaction as described below. The notary module receives these signed pending transaction objects and puts them in a queue for posting and sends them to the payment processing module for payment processing.

After the notary module receives the signed pending transaction objects, the payment processing module processes the payment indicated in the smart contract(s). For example, for an external gateway payment, once the notary module broadcasts a pending transaction object (that has been signed/confirmation by seller and buyer), the payment processing module processes the associated payment against the proper payment gateway. If instead payment is to be via a platform currency, the payment processing module requests/receives from the buyer MIDC 202 digital tokens from the account associated with the buyer identifier equal to the price indicated in the smart contract, and transfers the money/tokens to the owed parties (e.g. the account of the seller identifier and/or the system fee account). In some embodiments, the payment processing module ensures that all tokens/monies remain within the control of the operating system 206 and/or a central authority until a physical withdrawal is effectuated by a user. If one or more tokens, or fiat currencies, are stolen from a buyer and/or seller account, because all users are known because they must have been previously on-boarded and registered on a permissioned chain, the platform 102 is able to trace the tokens and record on the notary blockchain 206' that the tokens are no longer valid as well as replacing the stolen tokens in the account with newly minted tokens. In either case, if the payment is successful, the notary module then signs the pending transaction object (e.g. via the key module using a notary private encryption key) thereby forming a completed transaction object using the notary keys, and posts the completed transaction object as a single transaction block on the notary blockchain 206'.

The notary module then creates completed transaction confirmation blocks, signs each of the blocks using the notary private key (e.g. via the key module) and posts them as a single transaction block on each of the buyer and seller MIDCs 202 (appended to the blocks including the pending transaction objects). Thus, for each completed transaction, there will be two blocks posted to each of the buyer and seller MIDCs 202 (pending/initiated and completed transaction blocks) and one block posted on the notary blockchain 206' (completed transaction block). If the payment processing fails or the transaction is otherwise terminated after posting of the pending transaction object blocks, then no transaction block is added to the notary blockchain 206', and instead of the completed transaction, the notary module posts a failed transaction block (indicating what caused the transaction to fail) on the buyer and seller MIDCs 202. As described above, using a P-RAFT protocol, the processing/recordation of each of the (pending or completed) transactions/blocks on the notary blockchain 206' and/or MIDCs 202 is able to be assigned by the notary module to a particular horizontal partition of the notary blockchain 206' (and/or MIDCs 202) and performed by a node designated as the leader of that partition. In some embodiments, as described above, the platform includes a buffer memory pool that stores transactions that need to be recorded until the node to which they are assigned is ready to process/record them.

The completed transaction blocks (posted to the notary blockchain 206' and/or buyer and seller MIDCs 202) are able to be time-stamped, posted ordered and validated in real-time. In particular, unlike other blockchain systems, the notary module posts the block without first waiting for a full node consensus that the transaction is valid (e.g. not fraudulent). This enables the platform 206 to post transactions faster than any existing blockchain system resulting in greater throughput and efficiency of the platform 206. The posted block is able to indicate the terms of the transaction (e.g. price, date, payment, and other transaction data) or a reference to a smart contract for that transaction, as well as the seller and buyer encrypted unique identifiers (and/or the product identifier). Additionally, the transaction is posted as a single transaction block on the notary blockchain 206', the transaction is able to be later corrected by adding a new single transaction block to the blockchain 206' that indicates any necessary modifications to the original block. In some embodiments, the platform also effectuates the delivery of the product by digitally delivering the product to the buyer (e.g. buyer device 104) if a digital product or sends a message to the seller to deliver the digital or non-digital product to the buyer (e.g. buyer device 104 or buyer shipping address).

In some embodiments, the ledger module is used to maintain an account balance of one or more currency values on one or more of the user accounts. In such embodiments, upon completion of a transaction, the ledger module posts a new single transaction block on the buyer and seller MIDCs 202 indicating the adjustment to the existing account balance to the seller/buyer accounts on the seller and buyer MIDCs 202, respectively. Again, each of these transactions is added to their MIDCs 202 as a single transaction block (rather than multiple transactions in a single block) such that if there is a dispute or error, the single transaction block having the error is able to be corrected by a new updated single transaction block added to the MIDCs 202. For example, a fraudulent charge indicated in a first single transaction block on the MIDC 202 of the buyer is able to be corrected by a subsequent updated single transaction block (e.g. completed dispute block) crediting the charged amount back to the account (thereby correcting the indicated account total). This would not be possible if a single block was used for multiple transactions because the fraudulent transaction could not be corrected without also affecting all the other non-fraudulent transactions contained within that block. Alternatively, in the case where buyer/seller accounting is provided external to the platform 102, the ledger module and/or the MIDC 202 account balance blocks are able to be omitted.

At the same time as the pending transaction object signing, payment processed and/or posting of the completed transaction blocks (e.g. before, simultaneously or concurrently), the security module is able to perform a proof of transaction consensus process on the transaction in order to validate the transaction is not fraudulent or otherwise invalid. In some embodiments, the security module performs the proof of transaction consensus process by verifying that the buyer encryption keys used to sign the transaction are valid keys (e.g. that are associated with the encrypted buyer identifier using a hash verification of the keys). In some embodiments, the security module/engine includes artificial intelligence in order to aid in the speedy determination of consensus of each of the transactions. If the proof of transaction fails, the security module/engine notifies the notary module and the ledger module (if it is being implemented) so the notary module is able to post a new single transaction block correcting (e.g. nullifying) the transaction on the notary blockchain 206' and the ledger module is able to similarly post new single transaction blocks correcting the account balances of the seller and buyer on the seller/buyer MIDCs 202.

The dispute module receives transaction disputes from buyer and/or seller devices 104, 106 and resolves the disputes even after the single transaction block of the transaction has been posted to the notary blockchain 206' without compromising immutability of the blockchain 206'. Specifically, the dispute module operates as the central authority by determining if the smart contract conditions were met (e.g. payment made, product delivered) and adjudicates disputes and determine resolution adjustments (if necessary) to the disputed transaction. In response to receipt of a dispute request message from a user (e.g. buyer/seller) identifying a disputed posted transaction, the dispute module is able to generate and post pending dispute objects as single blocks on the notary blockchain 206' as well as the MIDCs 202 of the sellers, buyers and/or other entities that are a part of the transaction. In some embodiments, the dispute request message includes one or more of the transaction identifier, the buyer and/or seller identifiers (e.g. alphanumeric identifiers), the date of the transaction and/or other transaction data. These pending dispute blocks identify the disputed transaction in order to indicate to others inspecting the transaction (for any reason) that the transaction is currently disputed. Alternatively, the generation and posting of the pending dispute objects/blocks are able to be omitted.

Subsequently, in response to determination of the resolution of the dispute (e.g. as entered by an administrator; as indicated by a third party entity; as automatically determined by the dispute module programming), the dispute module generates and posts a completed dispute objects as single blocks on the notary blockchain 206' as well as the MIDCs 202 of the sellers, buyers and/or other entities that are a part of the transaction. These completed dispute objects are able to indicate changes to the identified transaction (if any) and confirm that the dispute has been resolved thereby correcting any previously posted block of the disputed transaction. For example, the completed dispute blocks are able to indicate one or more changes to the transaction including but not limited to: that the existing transaction values are verified (e.g. no changes were necessary); that the transaction is voided (returning funds from the seller to the buyer and rights to the product from the buyer to the seller); and that the transaction parameters are adjusted (adjusting the funds from the buyer to the seller or vice versa; adjusting a length of the transaction (e.g. a movie rental duration), and/or adjustments to any of the other transaction data of the transaction included in the completed transaction block). In such embodiments where the pending dispute blocks are omitted, if there are no changes as a result of the dispute resolution, the dispute module is able to refrain from posting any new blocks (because the existing blocks are still accurate as indicated by the dispute resolution).

As a result, related transactions (original blocks and subsequent corrections) are able to be readily grouped by and easily viewed on the chains 202, 206' as a "family" of blocks all related to the same transaction and or specific user, buyer or seller. Thus, the dispute module provides the benefit of being able to effectuate reconciliation of a dispute within the platform 102 without compromising the immutability of the blockchain 206'. Similarly, the platform 102 provides the benefit of being able to run transaction processing, validation and posting of ordered single transaction blocks in real-time (e.g. posting before consensus is complete) as well as providing dispute resolution in order to correct errors and/or fraudulent charges.

In some embodiments, the platform 102 implements a delayed block posting protocol comprising delaying the posting of one or more of the blocks to the target blockchains for a predefined delay period. In particular, this delay period is able to provide the advantage of ensuring that the blockchains are not poisoned by any blocks by adding time to determine whether the blocks are safe to post before posting them. The platform 102 enables the duration of the predetermine delay period for each of the blockchains to be manually input and/or automatically determined by the platform based on one or more of the source of the block (e.g. account identifiers, transaction identifiers), the type of blockchain (e.g. notary, MIDC), the type of block (e.g. pending transaction, completed transaction or other type of block as described herein), other data stored on the block as described herein, the network load, the processing power and/or the consensus results. In some embodiments, the platform 102 automatically dynamically adjusts the predetermined delay period during operation based on one or more of the above factors. As a result, each of the blockchains are able to have the same or different delay periods. In some embodiments, the delay is implemented before consensus for the block is determined. Alternatively, the delay is able to be implemented after the consensus is determined, but before the block is posted.

In some embodiments, the dispute module includes a loss mitigation function/engine (e.g. powered by artificial intelligence and/or machine learning) that monitors transactions submitted to the notary blockchain operating system 206 and identifies and stops suspicious transactions from being completed (e.g. from being recorded on the blockchains at all). In some embodiments, one or more of the modules involved in the purchase process are able to be combined. For example, in some embodiments the purchase modules is able to be a part of the authentication module/rosetta.

Operating Method

Figure 3:
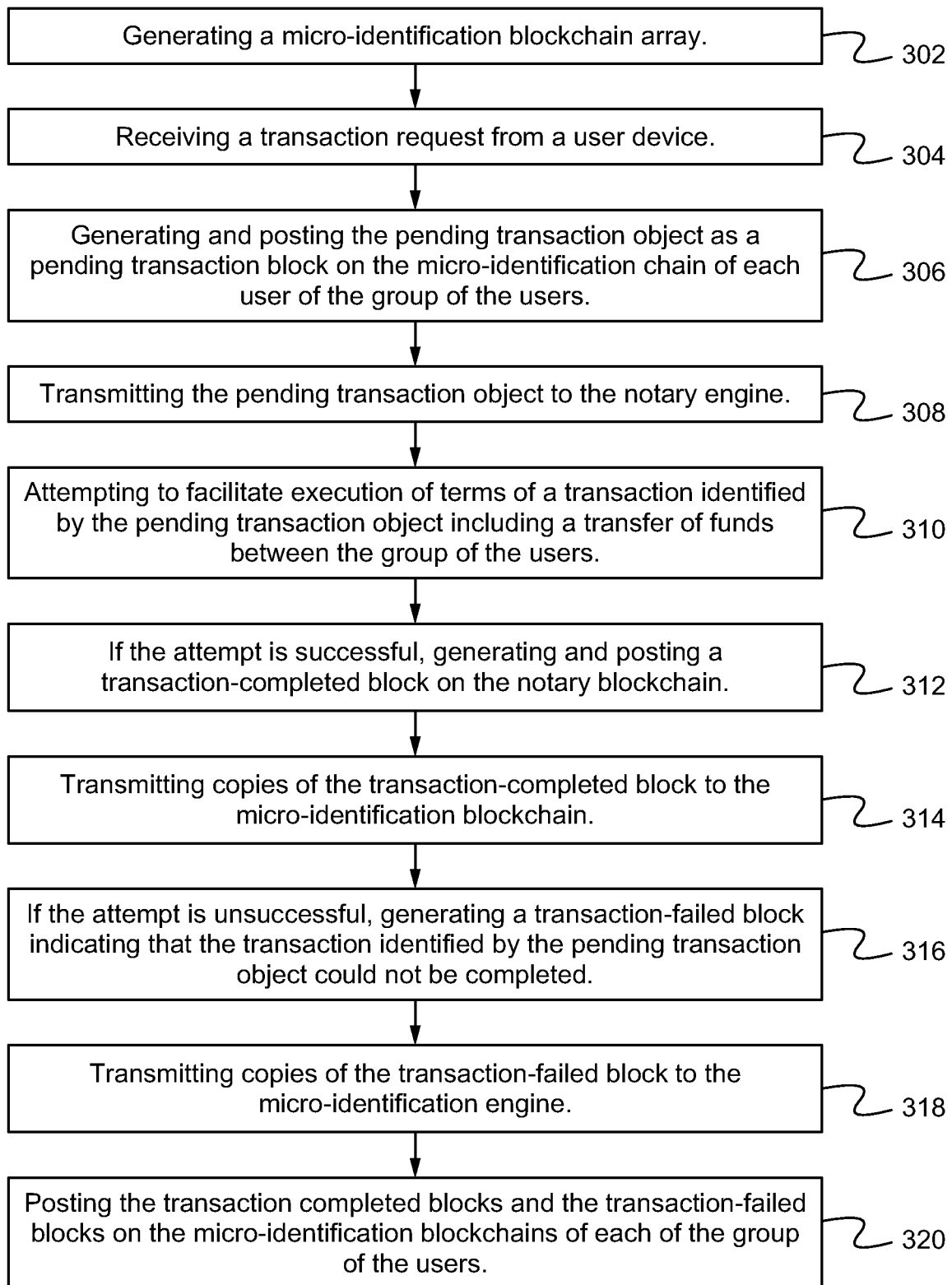
FIG. 3 illustrates a method of implementing a blockchain transaction platform according to some embodiments.

FIG. 3 illustrates a method of implementing a blockchain transaction platform 102 according to some embodiments. As shown in FIG. 3, a micro-identification engine of the blockchain transaction operating system generates a micro-identification blockchain array 204 at the step 302. In some embodiments, the array 204 formed by a stack of a plurality of micro-identification blockchains 202, wherein each one of the micro-identification blockchains 202 is dedicated to a single one of the users such that the one of the micro-identification blockchains 202 stores a native identifier of one of the users, a coded identifier of the one of the users and a set of personal information about the one of the users. The micro-identification engine receives a transaction request from a user device 104, 106 at the step 304. In some embodiments, the transaction request identifies a pending transaction object between a group of the users, wherein the pending transaction object is digitally signed by the private digital key of each user of the group. The micro-identification engine generates and posts the pending transaction object as a pending transaction block on the micro-identification chain 202 of each user of the group of the users at the step 306. The micro-identification engine transmits the pending transaction object to a notary engine of the operating system 206 at the step 308.

The notary engine attempts to facilitate execution of terms of a transaction identified by the pending transaction object including a transfer of funds between the group of the users at the step 310. If the attempt is successful, the notary engine generates and posts a transaction-completed block on the notary blockchain 206' at the step 312. The transaction-completed block indicates that the transaction identified by the pending transaction object is completed. The notary engine transmits copies of the transaction-completed block to the micro-identification blockchain 202 at the step 314. If the attempt is unsuccessful, the notary engine generates a transaction-failed block indicating that the transaction identified by the pending transaction object could not be completed at the step 316. The notary engine transmits copies of the transaction-failed block to the micro-identification engine at the step 316. The micro-identification engine posts the transaction completed blocks and the transaction-failed blocks on the micro-identification blockchains 202 of each of the group of the users upon receipt from the notary blockchain engine at the step 318.

In some embodiments, generating the micro-identification array 204 comprises generating each of the micro-identification blockchains 202 by generating a first block of the micro-identification blockchain 202 including the native identifier, the coded identifier and the set of personal information; encrypting the encoded identifier and the set of personal information; and generating and appending a second block to the first block, the second block including the coded identifier and the set of personal information as encrypted. In some embodiments, the notary engine is able to access blocks of the micro-identification blockchains 202 including the coded identifier and the set of personal information as encrypted, but restricted from accessing any blocks of the micro-identification chains 202 that include the native identifier. In some embodiments, the micro-identification array 204 is logically organized such that each of the micro-identification chains 202 form a logical row and an initial block of each of the stack of the micro-identification blockchains 202 form a logical first column and each subsequent block of each of the stack of the micro-identification blockchains 202 form logical subsequent columns.

In some embodiments, the method further comprises importing a database having stacked rows of cells of data with a block loader module by converting each row of the database into a new logical row of the array 204 formed by a new micro-identification blockchain 202 with each cell of the row of the database forming a new block of the new micro-identification blockchain 202. In some embodiments, the method further comprises, with the compliance module, identifying a geographic location of each one of the users when the users registered with the platform 102 and each time the users initiate a transaction on the platform 102; determining a set of stored data privacy rules that apply to the geographic location; and applying the set of data privacy rules to data added to the micro-identification blockchain 202 of the one of the users. In some embodiments, the method further comprises, in response to the one of the users selecting a right of erasure command, deleting the micro-identification blockchain 202 of the one of the users with the compliance module.

In some embodiments, the method further comprises, in response to the one of the users selecting a right of erasure command, storing a time that the command was received; determining an applicable set of the set of stored data privacy rules that apply to the one of the users and if the applicable set includes an erasure delay period; deleting the micro-identification blockchain 202 of the one of the users if the applicable set does not include the erasure delay period; and refraining from deleting the micro-identification blockchain 202 of the one of the users at the time that the command was received for the erasure delay period and deleting the micro-identification blockchain 202 of the one of the users after the erasure delay period has expired if the applicable set includes the erasure delay period. In some embodiments, the method further comprises determining if the pending transaction object includes illegal, malicious, cybersecurity compromising, hacking, phishing, malware or ransomware, type content and preventing posting of the pending transaction block if the pending transaction object includes illegal, malicious, cybersecurity compromising, hacking, phishing, malware or ransomware, type content with the anti-poisoning module. In some embodiments, the private digital keys are not stored on the platform 102 and the method further comprises dynamically regenerating the private digital keys with the key module upon request by one of the users. In some embodiments, the posting of the transaction-completed block on the notary blockchain 206' is performed before consensus for the transaction has been determined, the transaction-completed block including transaction data describing the transaction.

As a result, the method provides the advantage of providing MIDCs for storing user personal data and/or transactions thereby ensuring their safety over data stored on traditional databases while still enabling data privacy law and regulatory law compliance. Further the method provides the benefit of enabling transactions to be quickly posted before full node consensus has been determined while also being correctable due to each block only storing a single transaction such that errors are able to be corrected to subsequent single transaction correction blocks. This in contrast to other blockchain systems where full node consensus is required before blocks are able to be posted and thousands of transactions are stored on a transaction blocks containing multiple transactions such that to change an error on a block with a new single transaction block would require costly disruption of all of the other transactions that do not include an error on that block—which would also compromise the immutability of those existing chains due to their existing architectures. Further, the method provides the advantage of retaining the benefits of the immutability of the blockchains while still being automatically GDPR, CCPA and other data privacy law compliance and able to fully de-identify any user data/and or user stored private personal information at the request of the user without compromising the immutability of the systems on-chain blocks and blockchains. Moreover, the method provides the advantage of preventing block poisoning by implementing block screening before any block is posted on the notary chain 206' or MIDCs 202. Finally, the method provides the advantage of dynamically generating keys such that they cannot be phished from users or stolen from inside the platform 102.

Exemplary Device

Figure 4:
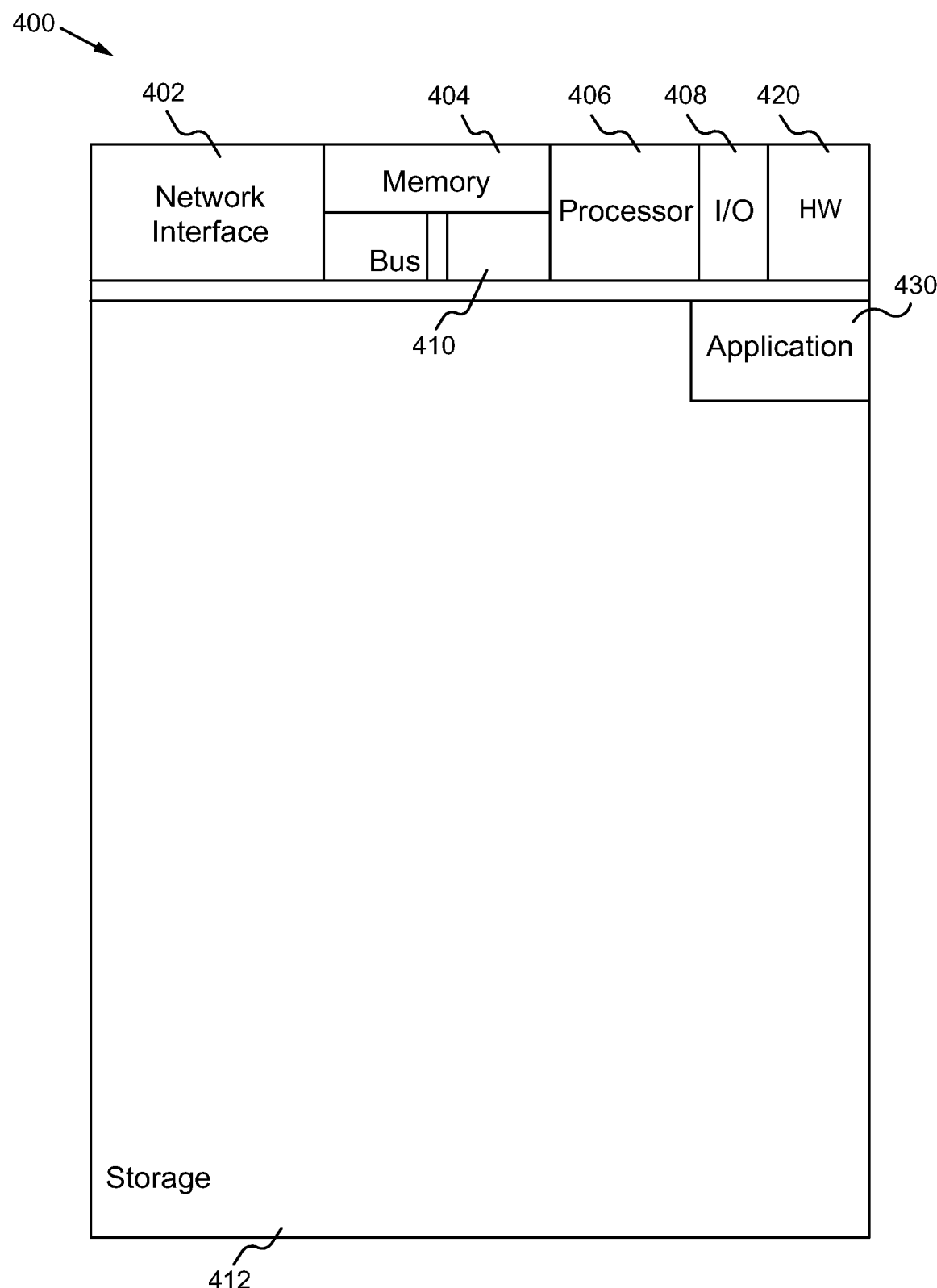
FIG. 4 illustrates a block diagram of an exemplary computing device according to some embodiments.

FIG. 4 illustrates a block diagram of an exemplary computing device 400 according to some embodiments. The computing device 400 is able to be one or more of the operating system 206, devices 104, 106, the blockchain 206' (e.g. each node of the blockchain 206') and/or any of the other electronic devices described herein. In general, a hardware structure suitable for implementing the computing device 400 includes a network interface 402, a memory 404, a processor 406, I/O device(s) 408, a bus 410 and a storage device 412. Alternatively, one or more of the illustrated components are able to be removed or substituted for other components well known in the art. The choice of processor is not critical as long as a suitable processor with sufficient speed is chosen. The memory 404 is able to be any conventional computer memory known in the art. The storage device 412 is able to include a hard drive, RAM, SRAM, CDROM, CDRW, DVD, DVDRW, flash memory card or any other storage device. The computing device 400 is able to include one or more network interfaces 402. An example of a network interface includes a network card connected to an Ethernet or other type of LAN. The I/O device(s) 408 are able to include one or more of the following: keyboard, mouse, monitor, display, printer, modem, touchscreen, button interface and other devices. The operating system(s), graphical user interface(s), application(s), module(s) and/or other software 430 used to operate the device 400 are likely to be stored in the memory 404 and/or storage device 412 and processed as applications are typically processed via the processor 406. More or less components shown in FIG. 4 are able to be included in the computing device 400. In some embodiments, hardware 420 is included. Although the computing device 400 in FIG. 4 includes software 430 and hardware 420, the features/functions of the system 100 and device 400 are able to be implemented on the computing device 400 in hardware, firmware, software or any combination thereof. Examples of suitable computing devices include a personal computer, a laptop computer, a computer workstation, a server, a datacenter, a mainframe computer, a handheld computer, a personal digital assistant, a cellular/mobile telephone, a smart appliance, a gaming console, a digital camera, a digital camcorder, a camera phone, an iPod™, a video player, a DVD writer/player, a Blu-ray™ writer/player, a television, a home entertainment system or any other suitable computing device. Further, it is understood that the system 100 and/or platform 102 is able to be deployed in single server or cluster of servers modes as well as on premises, data center, dedicated data center or via cloud computing environments and/or combinations thereof.

International Token Exchange Module/Engine

In some embodiments, the transactions are able to be initiated as a part of an International Token Exchange (ITX) module/engine. In particular, the ITX module is able to be an SEC and FINRA compliant module/engine (e.g. implemented using a downloadable or non-downloadable application, website, or combination thereof) to allow for the automated blockchain based trading and instant settlement of tokenized securities of any kind using the platform 102. As a result, the ITX module provides the benefit of being the only platform 102 capable of recording such transactions, along with buyer and seller PPI via the automated engine/platform that does so in a fully data privacy and regulatory law complaint manner.

In some embodiments, the platform 102 comprises an electronic learning data privacy law and regulatory law compliance module/engine that enables educational tools to seamlessly comply with data privacy and regulatory laws. Specifically, the compliance engine/module is able to function as middleware between schools and eLearning providers as an automated, real-time data privacy law and regulatory laws compliance engine. First, it ensures that the data and private personal information of the school's student population is always on-boarded, collected, curated, stored and deleted (when required) in compliance with all global, federal and state data privacy and regulatory law in an autonomous, 24/7, zero-trust manner. Second, it ensures that all student data is stored on its impenetrable and fully cyber-secured platform. As a result, that student data cannot be hacked, ransomed or phished.

Medical Status Module

In some embodiments, the operating system 206 is able to further comprise a medical status module (MS module) that uniquely enables a business, school, permissioned third party, or a company (or their human resource division), to interact with its employees, students or clients/users, on a private, secure, data privacy and regulatory law compliant level, to ascertain certain medical statuses of their employees/users. For example, the MS module is able to allow entities to determine if selected individuals have had, and passed, one or more tests or had certain medical procedures (e.g. Covid-19 active virus tests, antibody tests or vaccinations) in order to give the, the real-time daily knowledge of these individual's health statuses to allow the entities/users to safely populate their work environments (e.g. only with individuals who testing confirms them as to be not infectious). The MS module functionality is able to be implemented by the operating system 206 on the blockchain cluster, as a network-accessible website operating on one or more network servers of the system 100, as a downloadable application operating on the user devices 104, 106, or a combination thereof Registration In operation, a user or entity (e.g. company) accesses the MS module by using a web browser on their device 104, 106 to access the MS module implemented as a website and/or by downloading the MS module onto their device 104, 106 as a downloadable application. In some embodiments, upon creating an entity account, the MS module enables the entity to upload contact information (e.g. name, email, phone number, employee number/identifier, address or other identifying information) of one or more users that they wish to create user accounts on the platform 102 (and/or that will be associated with the entity account). The MS module subsequently transmits messages (e.g. text, email, telephonic) to devices of each of the identified users/employees/students. The messages are able to include text, video and/or audio indicating to download the MS module application and/or access the MS module website as well as one or more hyperlinks to the website and/or location where the application is able to be downloaded from.

In any case, the user or entity is able to create an account and MIDC 202 on the platform 200 using the registration module as described above. In some embodiments, the entity accounts are able to be associated with one or more user accounts, wherein the MS module enables the entity to access medical statuses of the associate user accounts and/or enables the associated users to broadcast their medical statuses to the entity account. For example, a company is able to create an entity account that is associated with the user accounts of its employees such that through the entity account the company is able to dynamically monitor and determine the medical statuses of each of its employees (e.g. covid negative, covid positive, unknown, fully vaccinated).

In order to facilitate this association of accounts, the MS module enables the entity to upload/submit identification information (e.g. email, phone number, address, employee number/identifier) of their employees and then the module uses the contact information to identify which user accounts to associate with the entity account. Similarly, the MS module enables users to upload/submit entity identification information to identify which entity to associate with the user account. In either case, the MS module is able to require confirmation by the identified user and/or entity accounts of their wish to associate with the identifying entity/user account before recording their association. Further, the MS module enables existing account associations to be terminated unilaterally upon request from the entity and/or user account.

All of these associations and terminations are able to be overseen by the privacy law and regulatory law compliance module, which as described above, determines the location of the users/entities, determines the applicable privacy/regulatory law, and obtains the needed permissions as well as handles the personal data according to the applicable privacy/regulatory law. For example, during the initial registration process for a user account (e.g. employee, teacher, student, etc.), the MS module captures all appropriate privacy and regulatory permissions (e.g. HIPPA) to allow the results of the relevant test and/or health data to be legally shared with the entity account (e.g. with the user's prior knowing opt-in permission).

Testing Function

Once the registration process is complete, the MS module provides a medical test function that enables users to select one or more of a plurality of available tests and procedures and then facilitates the taking of the selected tests/procedures. For example, the module is able to provide a list of an at-home Covid-19 (anti-body, antigen or other) test, a laboratory Covid-19 (anti-body, antigen or other) test, a Covid-19 vaccination procedure and other types of tests (Covid-19 related or non-Covid-19 related). Specifically, although Covid-19 tests/procedures and Covid-19 health statuses are described herein as examples, other tests/procedures and/or medical conditions are able to be used (e.g. sobriety tests, drug tests, lung capacity tests). In particular, the system is able to be used with any kind of medical condition/status, health data and/or medical test/procedure (wherein results of the test/procedure are able to indicate a medical status). As a result, the statuses for any user/account are able to be a combination of statuses depending on the results of each of the tests taken by the user.

In some embodiments, if the selected test/procedure is an at-home test/procedure, the MS module is able to automatically order the test materials for delivery to the user. For example, the MS module is able to use payment and address information submitted during the registration process to pay for the test materials and enter the shipping address (with confirmation from the user). In some embodiments, if the selected test/procedure is an out-of-home test/procedure, the MS module is able to facilitate an appointment for the user for approved testing at a desired facility, or a with a telemedicine provider. In some embodiments, the MS module dynamically determines and is capable of providing various information including logistics and information as to test/procedure locations and/or directions thereto, or how to order tests. In some embodiments, the MS module is also able to process and order such testing supplies, and process direct, third party or insurance payment for same. In some embodiments, the MS module is also capable of tracking delivery, usage and when refill is due.

After receiving selections of one or more of the provided tests/procedures, the MS module facilitates and/or provides instructions on how to take the test/receive the procedure. If the selected test/procedure is a laboratory (e.g. not at-home) test/procedure, the MS module is able to generate and issue a unique user identifier (e.g. a bar code, QR code, alphanumeric string and/or other identifier) to the user that they are able to access on their device 104, 106 upon submitting to an ID verification process (e.g. using the biometric lock module). In particular, the user identifier is able to be associated with the user and the selected test/procedure (e.g. stored in a unique identifier table one the user device 104, 106 and/or on the servers/nodes running the operating system 206) such that upon receiving test results (indicating medical statuses) along with the unique identifier, the module is able to determine which MIDC to add the updated medical statuses to.

Accordingly, at the testing facility, once the user has logged onto and/or validated their identity with the MS module, the module enables the user to access and/or display the unique identifier for the test on their device and/or transmit the identifier to facility (e.g. via email, text or other media). In some embodiments, the user validates their identity on the MS module on their device using their biometric data (e.g. voice, fingerprint, face, etc.) via the biometric lock module described above. For example, the module is able to access a stored image of their driver's license (or valid school and/or parental ID) and compare it to a live captured facial image to verify the user's identity as the proper test taker. Alternatively or in addition, the user is able to validate their identity using their username and password and/or other identifying data submitted during the registration process.

Subsequently, the user is able to provide the unique identifier to the medical facility, laboratory or point of care facility, which is able to transmit the relevant medical data or results along with the unique identifier to the MS module on the platform 102. Upon receiving the test results along with the unique identifier, the MS module updates the MIDC 202 of the user identified by the unique identifier with a transaction on a PPI update block that includes the medical data/results (in the same MIDC update manner described above). Further, in the same manner as described above, an anonymized version of the update block is able to be recorded on the notary blockchain. As a result, the MS module provides the advantage of enabling the test results of the lab test to be validated such that it can be later provided by the user in order to prove their medical status. In some embodiments, for example in conjunction with the tokenization module described below, the platform 102, notary block chain and/or MS module is able to generate a digital certificate of authenticity for the PPI update block for subsequent transmittal to and verification by a data validator node. In some embodiments, the digital certificate of authenticity is able to be the unique identifier associated with the test and the user and/or a different identifier/signature associated with the block/user.

If instead, the test is an at home test, the MS module on the user's device (e.g. computer, smartphone, etc.) is able to re-validate the individual's identity as described above and then continuously monitor (e.g. via object tracking with the device) the individual during the test to ensure that they are the ones who actually submit the testing sample. If the MS module is unable to continuously monitor the user during the test, the module is able to not accept the results of the test and/or transmit an alert to the user to revalidate or the results will be rejected. If accepted, after receiving the results (e.g. as captured from an image of the testing material), the MS module is able to transmit the test results/medical status along with the identifier of the user (e.g. alphanumeric identifier assigned during registration) to the platform 200 which records the results/medical status on the MIDC 202 of the associated user/user account as a transaction on PPI block or PPI update block in the same manner as described above. Further, an anonymized version of the update block is able to be recorded on the notary blockchain.

Again, as with the "out of home" facility tests described above, the platform 102, notary block chain and/or MS module is able to generate a digital certificate of authenticity for the PPI update block for subsequent transmittal to and verification by a data validator node, wherein the digital certificate of authenticity is able to be the unique identifier associated with the test and the user and/or a different identifier/signature associated with the block/user.

Validity Time Periods

In some embodiments, instead of just storing and updating the medical status data of each of the users, the MS module is able to automatically assign one or more of the determined statuses of a person a validity time period, wherein upon expiration of the time period that status is able to automatically change to another status or be removed entirely. The duration of the validity time period is able to be based on the status and/or test that indicated the status. Specifically, the duration is able to be determined based on the time of the test and parameters of the type of status (e.g. quarantine periods, antibody duration, vaccine durable immunity, testing supplies, medication quantity supplied, and/or other characteristics that indicate an expected duration of the status). For example, if a covid-free status was obtained from a daily home rapid covid-19 active virus test, the MS module is able to assign the status a 24 hour validity time period, and upon expiration of that period, the module would change the user's covid-19 status from covid-free to unknown. Similarly, if a covid-free status was obtained via a vaccine administration, the validity time period is able to be 3 months or another durable immunity time period that the vaccine is estimated to provide before the module automatically changes the user's status back to unknown.

In some embodiments, the entity accounts associated with the user accounts are able to view the validity periods along with the associated statuses such that they are able to know when a current status is set to expire. In some embodiments, the MS module is able to adjust the duration that it assigns to one or more of the validity periods based on one or more factors such as changed guidance from governmental or scientific authorities on the status. In some embodiments, these validity time periods are stored on the MIDC 202 along with the medical status information. Alternatively, the validity time periods are able to be stored elsewhere on the platform 102. In some embodiments, upon expiration of a status, the MS module updates the MIDC 202 of the user with an updated PPI block reflecting the change in status. Alternatively, the MS module is able to refrain from updating upon expirations (e.g. because the expiration status is indicated by the current time being beyond the expiration time indicated on the MIDC block) and instead only update the MIDC 202 of the user when status changes occur separate from the expiration of the validity time period. In some embodiments, the user medical status is updated on the MIDC 202 in real-time whenever a change occurs. Alternatively, the status is able to be updated at specified times, a specified frequency, upon receiving a command from a user and/or upon reconnection of the user device 104, 106 to the platform 102 (e.g. if the device is temporarily disconnected).

The MS module is also able to warn/notify the user or permissioned parties when the expiration of the validity time period is imminent. For example, the module is able to automatically send reminders (e.g. texts, emails, and/or phone calls) to users devices 104, 106 when one or more of their current statuses is set to expire within one or more years, months, weeks, days and/or hours. The messages are able to indicate the status, when the status is set to expire and/or how to reset/extend the status.

Status Display Function

At the same time as it is managing the statuses of a user/account, the MS module provides a display function that enables the user (and/or the entity account associated with the user) to access, transmit and/or display one or more of its current statuses. For example, the display function enables the user/entity to select one or more of the current statuses (as indicated by the most updated PPI block on the user's MIDC 202), and generates a status display in the form of one or more images, messages/signals and/or files that identify the user (e.g. via an image of their face, name, platform user identifier, employee number or other identifying data), the selected statuses and/or the validity period/ expiration time of the statuses. The status display is able to be transmitted as a file to the user/entity (e.g. text, email), displayed on a webpage (e.g. a dashboard website/portal operating locally on a company/school/business/permissioned third party's system and/or remotely via one or more platform associated servers), transmitted to an electronic display (e.g. one or more tags, badges, signs or other indicating devices), displayed on the user device 104, 106 (e.g. on the downloadable application of the MS module), and/or otherwise provided to the user/entity. For the electronic network connected displays, the MS module is able to provide continuous or periodic status displays that are dynamically updated (e.g. in real-time) to reflect updates to the MIDC 202 of the user (due to user status changes).

For example, in the case of medical statuses related to covid-19, the display function is able to allow human resources at a company, a school or permissioned third party to see their employees', students', or users' real-time Covid-19 tests results (e.g. the medical statuses related thereto) all in a user permissioned and privacy law compliant manner. In such embodiments, the display function is able to use a plurality of colors to represent the covid-19 status of the user on the status display. A first color, such as red, is able to indicate one or both of covid-19 virus present or unknown. A second color, such as yellow, is able to indicate covid-19 testing or testing results pending. A third color, such as green, is able to indicate covid-19 free. In some embodiments, one or more of the colors also include one or more subcategories. For example, third color subcategory A is able to indicate Covid-19 antibodies present, third color subcategory V is able to indicate the user has had a Covid-19 vaccination, and third color subcategory T is able to indicate the user daily tested as negative for active Covid-19 infection.

Using these classifications individuals would have their status visibly demonstrated, with their permission, and displayed by the display function using a colored background behind the individual's picture in the status display. For example, a person with an active infection or has had no prior testing is RED status. The system would show them with a RED background displayed behind their picture on the graphical user interface of the application and/or website. Further, a user that has had a test, but where the lab results are still pending is able to have a different indicator (e.g. a YELLOW background displayed behind their picture). Users that have had a positive antibody test, tested daily with a rapid covid-19 active virus test as negative or had a covid-19 vaccination would have a GREEN background displayed behind their picture—along with the letters A, V or T to show the specific type of Green status they have.

Contact Tracing Function

In some embodiments, the MS module includes a contact tracing function that upon receiving a medical status of a user, is able to automatically send a possible exposure message to potential contacts. Further, the contact tracing function is able to determine locations where the user has recently visited and/or other individuals who have been in contact with that user or in those locations. For example, when a user is identified as having a status (e.g. Covid-19 or another contagious illness), the MS module is able to automatically access email and/or phone number contact information (e.g. parsed from the user device 104, 106 executing the MS module and/or manually input by the user via the MS module graphical user interface) and send possible exposure alerts (e.g. via text, email and/or phone messages) to each of the contacts indicating the illness and the possible exposure. The source of these alert messages are able to be anonymous and only performed with user preconfirmed permission. As a result, the contact tracing function provides the advantage of allowing for a positive tested individual to have alerts sent to their contact list—without ever identifying them as the person who was infected, or them having authorized the alert to be sent—totally protecting their identity and privacy.

As another example, the contact tracing function is able to determine locations and times where the users have recently visited using data accessed from the geo-location and geo-fencing of their user devices 104, 106. As a result, when an infectious user status is determined/input by the MS module and/or platform, the MS module is able to determine a number of locations and a time at the location that the infectious user has been within predetermined time period (wherein the time period is based on the medical status), check if any other of the users have been in the same locations at the same times (within a predetermined buffer period) and send possible exposure messages to each of the user's that were in one of the number of locations proximate the times that the user having the infectious status was. Indeed, this contact tracing function provides the advantage of not only determining if there was direct contact between two individuals, but also determining if an individual visited a location where an infected person was recently (even if not there anymore). In some embodiments, the contact tracing function utilizes triangulation of multiple location vectors (e.g. Bluetooth beacons, GPS and Wi-Fi) for even more precise location analysis down to a granular floorplan level for individual locations.

Location Risk Map

In some embodiments, the MS module is able to further comprise a location risk map function that indicates location/entity risk status of one or more of the entities/locations displayed on the map based on the medical status of the employees of the entity and/or if any users having an infectious status have visited the location/entity within a predefined time period. In particular, the function is able to periodically or upon demand update the risk status of each of the locations/entities on the map to provide the most up to date data on the map location/entities. For example, a retail store itself is able to be indicated as having a safe or "green" risk status if all of the employees have been tested and are determined by the system as also being non-infectious (and/or the customers who have visited the store recently). In some embodiments, triangulation of multiple location vectors (e.g. using Bluetooth beacons, GPS and/or Wi-Fi) allows for even more precise location analysis down to a granular floorplan level for individual locations. In some embodiments, when displaying the map, the MS module enables the user to select one or more from a list of medical risks/statuses (e.g. covid-19, influenza, etc.) from which the risk status of the displayed location/entities is chosen. In other words, risks related to the selected statuses are considered when assigning the risk status, whereas those that are not selected are ignored for the purposes of determining risk status.

As a result, these company/location risk statuses are able to be used to guide consumers as where it is safe to shop, eat and otherwise visit. In some embodiments, this risk status presentation and/or dynamic updating is able to be implemented on any connected device that the platform/engine/module/application is able to access (or be executed on) and thus provide the status information to. As described above, this is able to include phones, computers, internet of things devices, employee badges, identification cards, billboards and/or any device that is able to be accessed by the platform.

Figure 10:
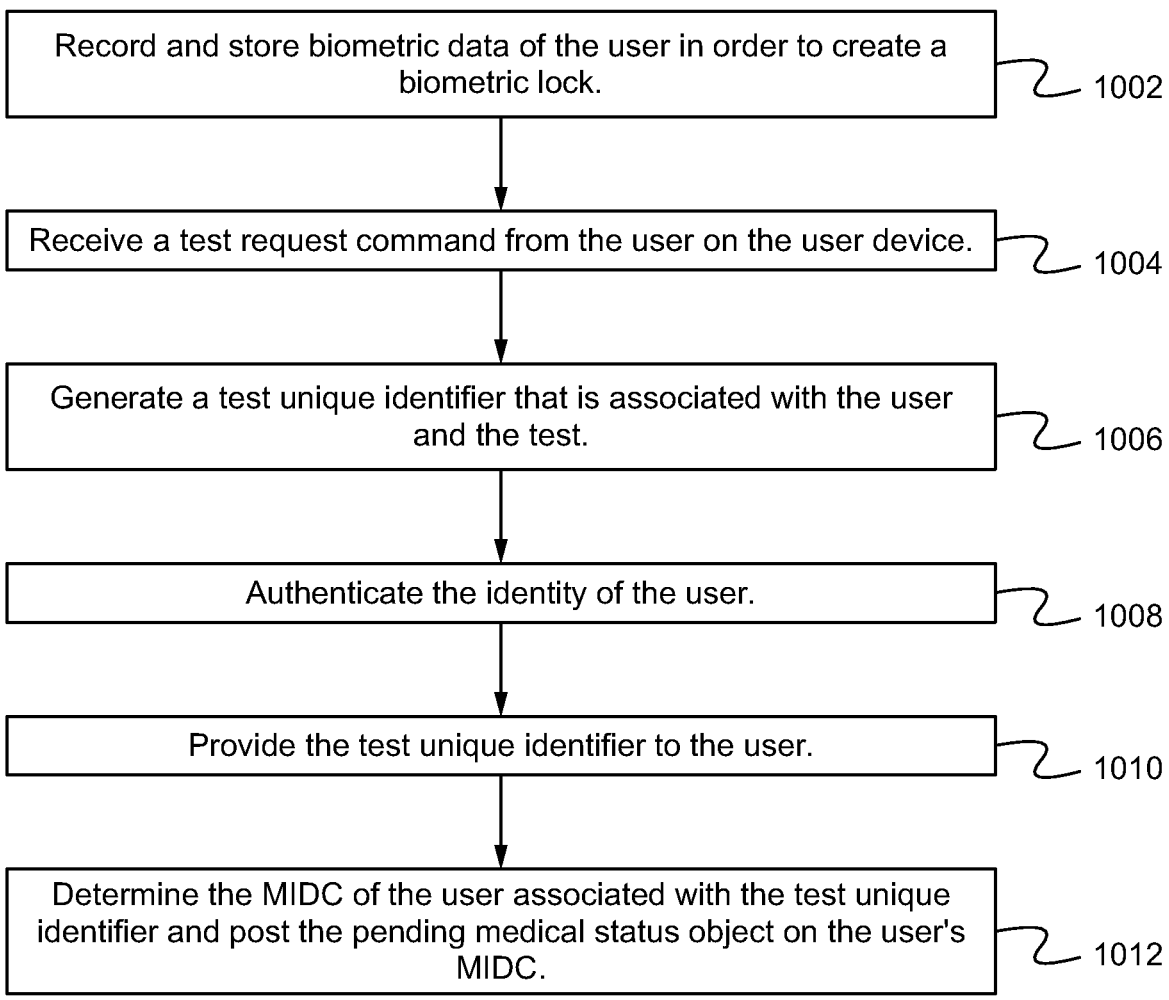
FIG. 10 illustrates a method of implementing a medical status module according to some embodiments.

FIG. 10 illustrates a method of implementing a medical status module according to some embodiments. As shown in FIG. 10, the MS module records and stores biometric data of the user in order to create a biometric lock at the step 1002. The MS module receives a test request command from the user on the user device 104, 106 at the step 1004. The request is able to be for a lab test or an at-home test. If the request is for a lab test, the MS module generates a test unique identifier that is associated with the user and the test at the step 1006. The test unique identifier is able to be in the form of an alphanumeric string, a bar code, a QR code or other format. The MS module authenticates the identity of the user at the test site using the biometric module at the step 1008. For example, the MS module is able to determine if the stored biometric data of the user matches current measured biometric data (e.g. voice data, facial image data, fingerprint data) input by the device 104, 106. If the user identity is authenticated, the MS module provides the test unique identifier to the user on the device and/or directly to a device at the test facility at the step 1010.

Alternatively, if the test was an at-home test, the MS module is able to verify the identity of the user using the biometric module (e.g. biometric lock) and then continuously monitor that the user stays within a field of view of a camera of the user device 104, 106 from the time when the identity of the user is authenticated until the at-home test is taken thereby ensuring the test was taken by the identified user. The MS module is then able to visually, electronically, or otherwise capture results of the at-home test (depending on the type of at-home test). As a result, the test unique identifier and the test results are able to be transmitted to the operating system 206 (either directly from a test facility device or via the user device).

Upon receiving the test unique identifier and test results as a medical status transaction request identifying a pending medical status object, the operating system determines the MIDC 202 of the user associated with the test unique identifier and posts the pending medical status object as a single transaction block on the user's MIDC 202 at the step 1012. Thus, the method provides the advantage of ensure the provenance of the test results such that the user is able to use them to prove their medical status at the work place and elsewhere.

In some embodiments, the operating system 206 assigns an expiration date to the medical status stored on the MIDC 202 based on an expected duration of the medical status and when the test was administered. Specifically, the operating system 206 is able to calculate when the medical status will no longer be valid by adding an expected duration of the medical status to a time when the test was administered. In some embodiments, the MS module generates and provides a reminder message to the user on the user device 104, 106 when a current time is within a threshold range of the expiration date of the medical status. In some embodiments, upon receiving a request to display the medical status of the user, the MS module generates and displays a status image that indicates the current medical status of the user (e.g. the tested status and when that status is set to expire; or that the latest status is no longer valid because it has expired). Alternatively, the MS module is able to automatically display the status image and changes thereto without request (e.g. on an ID badge or other networked device as described above).

In some embodiments, the MS module generates a map on the user device 104, 106 indicating the location and status of one or more entities (e.g. all employees having a desired medical status, one or more employees not having a desired medical status or having an unknown status). Similarly, in some embodiments, the MS module generates a risk map on the user device 104, 106 that indicates locations where a person having one or more undesirable medical statuses has recently visited (e.g. within a selected time frame). In particular, the MS module is able to determine the user's having the undesirable statuses based on the stored medical statuses on their MIDCs 202 and the locations they have visited within the selected time frame based on their device 104, 106 location during that time and display that information on the map so that others may assess their risk and/or avoid those locations.

Token Ecosystem Module

In some embodiments, the operating system 206 of the platform 102 comprises a token ecosystem protocol that establishes a platform cryptocurrency token (e.g. platform tokens) wherein users (e.g. buyers, sellers, users, entities) are able to use the platform token to not only purchase and access services/goods (e.g. testing services, testing goods, authentication services and/or other goods/services described herein), but also to stake their platform tokens (or other types of tokens) in order to be chosen, or participate in data validator (DV) nodes (such as those of the MS module above) as well as voting, governance and/or reward functions described herein. In some embodiments, the token ecosystem protocol implements a non-custodial service for its initial staking through Delegated Proof of Stake (DPoS) tokens. In such embodiments, by utilizing and working with cryptocurrencies that are DPoS, the platform 102 provides the benefit of reducing security risk as it does not handle any of its users digital assets, but rather lets them remain in the user's custody. Alternatively, the token ecosystem protocol is able to implement other initial staking procedures.

A staking function of the protocol enables users to pay/submit/stake their platform tokens or certain other coins/tokens to run data validator nodes. Every transaction on the data validator node causes the staking function of the protocol to pay a small amount of gas in the platform token itself. Part of this gas is bought back by the staking function paid for in a secondary token (e.g. parachain token) to provide gas for writing the final blocks to the parachain's shared state as described below. The remainder of the gas is paid back to stakers as a reward. The cost of buying back the platform tokens as part of utilizing the validator node is able to be factored into the cost of the platform itself for end-users. In this way, the tokenomics of the system is designed to thank and reward token holders for their early support by decreasing the circulating supply of the token while maintaining a steady demand, creating instant and ongoing value for the token itself. Additionally, in some embodiments the protocol provides periodical a pool reward, wherein upon selection of a user to burn one or more platform tokens the users are provided one or more entries into a reward pool. Subsequently, at the periodical times, the protocol automatically randomly selects one or more of the entries and provides a reward to the accounts of the users, such as, a predetermined amount of platform tokens and/or other types of tokens.

Further, a governance function of the token ecosystem protocol is able to enable permissioned users to submit proposals, vote on submitted proposals and/or otherwise adjust the operation of the protocol. Specifically, the protocol determines which of the users holds and has staked one or more platform tokens and enables those users to input proposals, provide submitted proposal descriptions to the users, and enables the users to input votes (e.g. yes or no) on the proposals. In some embodiments, each staked platform token of a user enables the user to submit one vote. Alternatively, each staked platform token is able to equate to more or less than one vote (e.g. ½ a vote meaning that at least two staked tokens are required to submit a vote). In some embodiments, in addition to being determined by the protocol as being permitted to submit proposals, in order for the proposal to be accepted the user must also submit a number of platform tokens equal to a collateral value (e.g. $100, 75 tokens, or other values).

If the proposal should fail (e.g. because a governance council votes against it and/or it receives less than 51% or another threshold percentage value of the total votes voted for the proposal), the user loses their submitted collateral. Alternatively, if the proposal succeeds (e.g. because the governance council votes for it and/or it receives more than 50% or another threshold percentage value of the total votes voted for the proposal), then the governance function returns the collateral to the account of the user and/or as well as an additional amount of platform tokens for helping the ecosystem. In some embodiments, the governance function enables the submission of proposal on topics including, but not limited to: pricing changes (e.g. services, health data), node reward percentage changes, future issuances/splits, token burns quantity and timing based on token performance, changes in token interest rates, platform token inflation levels, platform grants, whether to add additional staking assets, data validator node gas prices, data validator node DOT re-staking and parachain leasing, or other topics.

For example, a user is able to propose the setting and adjustment of rates for subscriptions to transaction data (e.g. health data subscriptions as described herein) and one-time use of the transaction data (of transactions stored on the platform 102). For example, the transaction data is able to be user permissioned health data, or attestation of health data accessed by various entities for verifying health data of one or more users/employees/passengers. In such embodiments, to ensure that health data, test results and attestations of health status via transaction data stored on the platform can be trusted, each individual test's certificate of authenticity (as digitally recorded on the platform notary blockchain) is be verifiable by the community.

Figure 11:
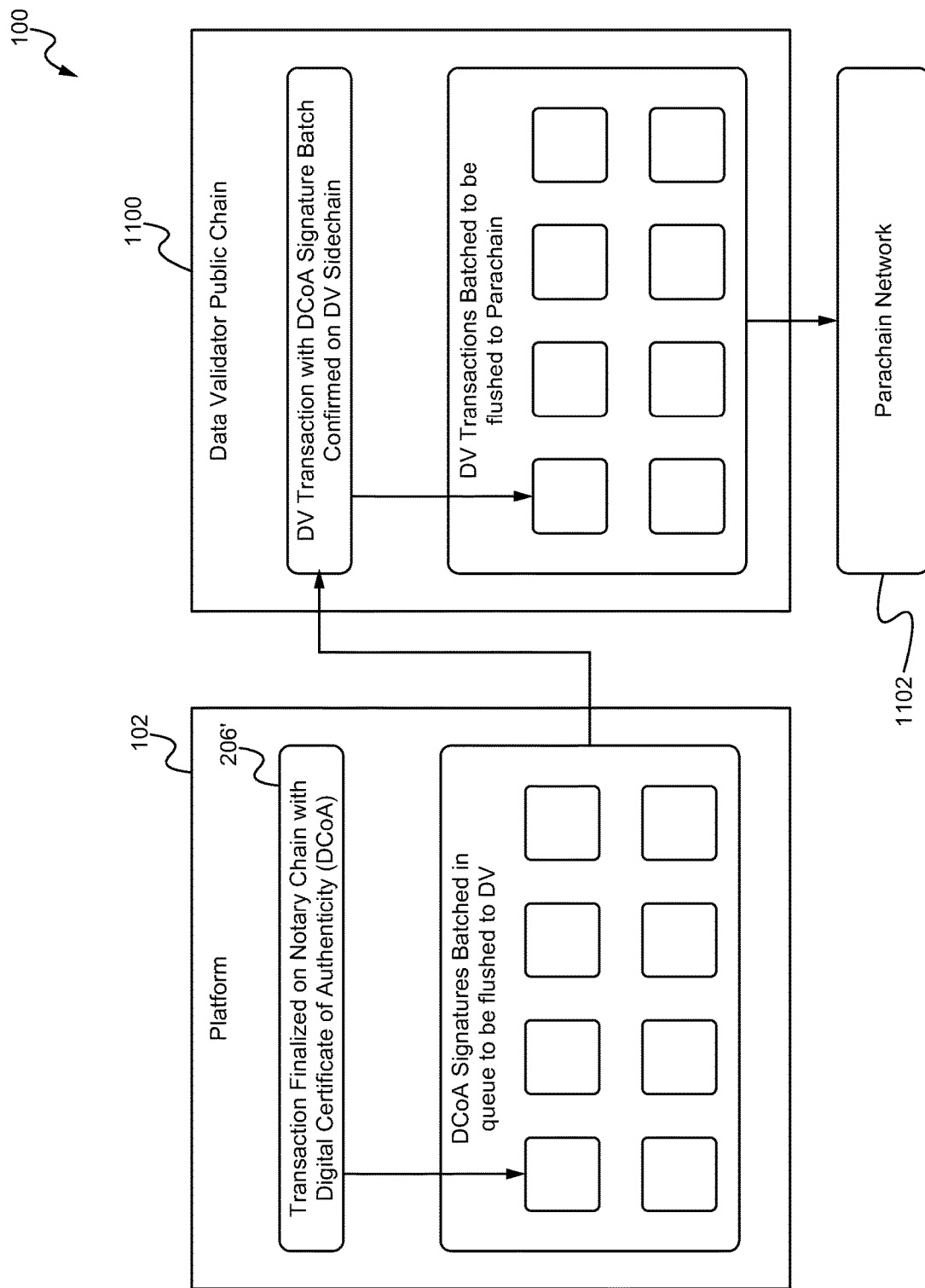
FIG. 11 illustrates the system including the token ecosystem module according to some embodiments.

FIG. 11 illustrates the system 100 including the token ecosystem protocol according to some embodiments. The system of FIG. 11 is able to be substantially similar to the system 100 of FIG. 1 except for the differences described herein. As shown in FIG. 11, the system 100 includes a DV public blockchain or sidechain 1100 coupled between the platform 102 and a parachain or parathread network 1102. In operation, when transaction data (e.g. health data, sales data) is collected and stored as described above, every resulting transaction is recorded on the platform's notary substrate blockchain 206' and/or MIDC 202 with a digital certificate of authentication (DCoA). Subsequently, a signature of these DCoAs and the transactions are sent as batches to a selected one of the DV nodes of a sidechain of the substrate, which confirms each of the transaction/signatures are valid on the sidechain 1100. After confirmation on the sidechain 1100, the transactions/signatures are then able to be sent to the parachain network 1102 where they are recorded together as blocks on a parachain blockchain for future use in presenting transaction data indicated by the transactions and certified by the DCoAs.

In operation, under the token ecosystem protocol, the gas for recording each of the transactions and/or providing the DCoA on the platform substrate blockchain 206' and/or MIDC 202 is paid for by the user associated with the transaction using the platform tokens paid to the DV node used to validate the DCoA/transaction. After the transaction is completed and authenticated by the selected DV node on the sidechain 1100, part of this gas (i.e. platform tokens) is bought back from the DV node by the platform 102 using a second cryptocurrency token (e.g. parachain network 1102 token). The DV node then provides this second token to the parachain 1102 as secondary gas for writing the final blocks (including the validated transaction/DCoA) to the parachain 1102 (e.g. using a network protocol that allows arbitrary data and tokens to be transferred across blockchains). The remainder of the first gas provided to the DV node is able to be paid back to the users that are currently staking that DV node (using the staking function) that authenticated the transaction/DCoA on the sidechain 1100 as a reward. Thus, the token ecosystem provides the advantage of incentivizing users to buy the platform tokens and/or stake the DV nodes.

Figure 12:
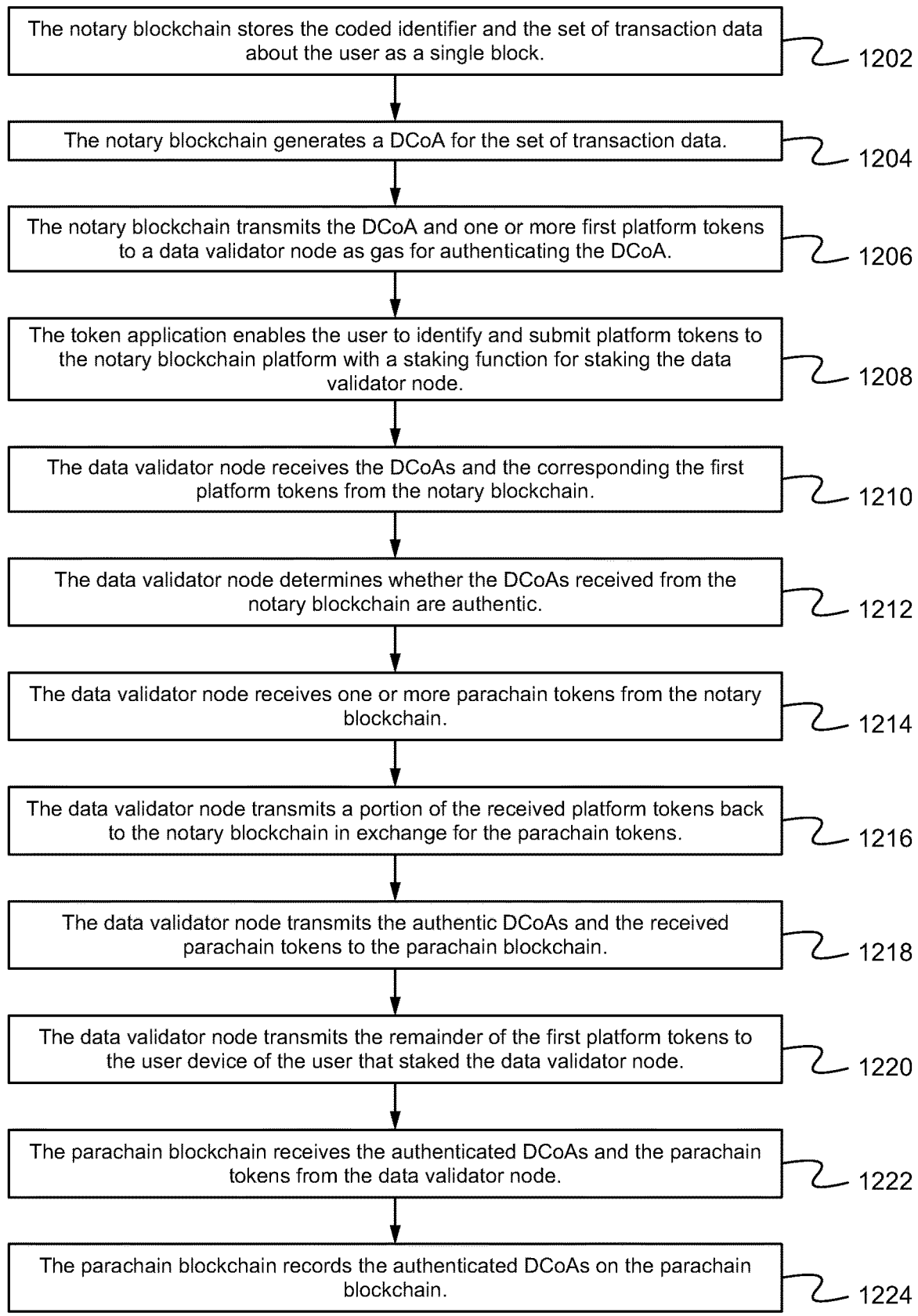
FIG. 12 illustrates a method of operating the token ecosystem module according to some embodiments.

FIG. 12 illustrates a method of implementing the token ecosystem module according to some embodiments. As shown in FIG. 12, the notary blockchain (and/or MIDC) stores the coded identifier and the set of transaction data about the user as a single block at the step 1202. In some embodiments, a new single block is stored (on the notary chain and/or MIDC) each time the set of transaction data is updated. In some embodiments, the single block on the MIDC includes the native identifier of the user, but the single block in the notary blockchain does not include the native identifier so the user remains anonymous on the notary blockchain. The notary blockchain generates a digital certificate of authenticity for the set of transaction data at the step 1204. In some embodiments, new certificate is generated each time the set of transaction data is updated. The notary blockchain transmits the digital certificate of authenticity and one or more first platform cryptographic tokens to a data validator node as gas for authenticating the digital certificate of authenticity at the step 1206. The token application enables the user to identify and submit platform tokens to the notary blockchain platform with a staking function for staking the data validator node at the step 1208.

The data validator node receives the digital certificates of authenticity and the corresponding the first platform cryptographic tokens from the notary blockchain at the step 1210. The data validator node determines whether the digital certificates of authenticity received from the notary blockchain are authentic at the step 1212. The data validator node receives one or more parachain tokens from the notary blockchain at the step 1214. The data validator node transmits a portion of the received platform tokens back to the notary blockchain in exchange for the parachain cryptographic tokens at the step 1216. In some embodiments, the value of the portion of platform tokens is equal to the value of the parachain tokens. The data validator node transmits the authentic DCoAs and the received parachain tokens to the parachain blockchain at the step 1218. The parachain tokens are able to be gas for recording the digital certificates of authenticity on the parachain blockchain. The data validator node transmits the remainder of the first platform tokens to the user device of the user that staked the data validator node at the step 1220. The parachain blockchain receives the authenticated DCoAs and the parachain tokens from the data validator node at the step 1222. The parachain blockchain records the authenticated DCoAs on the parachain blockchain at the step 1224.

In some embodiments, the token application provides a rule proposing function to the user via a graphical user interface of the device, the rule proposing function enabling the user to enter a rule that indicates an adjustment to the blockchain platform. As described above, these rules are able to comprise one or more of a platform cryptocurrency token interest rate value, a platform cryptocurrency token inflation value, and a quantity of platform cryptocurrency tokens required by the data validator node to validate one of the digital certificates of authenticity. Further, in some embodiments, the token application provides a voting function to the user via a graphical user interface of the device. In such embodiments, the voting function is able to identify a set of the users that are currently staking at least one of the platform cryptocurrency tokens using the staking function, provide each of the rules proposed using the rule proposing function during a period, and enable the set of the users to submit at least one vote for or against each of the rules proposed. In some embodiments, each user has a number of votes equal to the number of tokens they have staked. Alternatively, each user is able to have a number of votes greater than or equal to their number of staked tokens, with the number of votes being proportional to the number of staked tokens.

In some embodiments, for each of the rules proposed the voting function adjusts the operation of the platform 102 according to the adjustments indicated by the rule if and refrains from adjusting the operation of the platform 102 according to the rule if the votes for the rule do not exceed the votes against the rule. In some embodiments, the staking function is able to store and update a staking table identifying each of the users currently staking the platform tokens and indicating an amount of the platform tokens that the user is currently staking. This table is able to be stored on the user device, on the notary blockchain (and/or the blockchain servers), on the data validator nodes or elsewhere in the platform as long as it is accessible by the voting function. In some embodiments, the token application requires payment of predetermined quantity of platform tokens (e.g. a number of tokens and/or a monetary value that the quantity of tokens need to equal) before enabling the user to enter the rule. In some embodiments, the token application refunds the predetermined quantity of platform tokens back to the user if the votes for the rule exceed the votes against the rule and/or provides a reward of extra tokens for contributing to the token ecosystem. Thus, the method provides the advantage of encouraging user participation in the token ecosystem.

Decentralized Health Information (DeHI) Module

In some embodiments, the operating system 206 is able to further comprise a DeHI engine or module that uniquely enables users to convert their electronic health records (EHR) into non-fungible tokens (NFTs) that are able to be stored on their MIDCs 202 and/or represented on the notary blockchain 206' to ensure their authenticity. Further, the DeHI module enables users to selectively share their electronic health records with medical providers and/or other entities as permitted by the user in exchange for compensation to the user and/or the platform 102. At the same time, it allows users of health data to align their interests with token holder interests.

The DeHI module is able to comprise a program, service, function, website and/or downloadable application that operates in cooperation with the platform 102 in order to create, record, maintain and/or share the electronic health record non-fungible tokens (EHRNFTs) with medical providers or other entities. The DeHI module functionality is able to be implemented by the operating system 206 on the blockchain cluster 206', as a network-accessible website operating on one or more network servers 102 of the system 100, as a downloadable application operating on the user devices 104, 106, or a combination thereof. In some embodiments, the DeHI module is able to be combined with and/or work in cooperation with the token ecosystem module described above such that the DeHI module is able to establish a platform cryptocurrency fungible governance token, wherein users are able to use the governance token to not only purchase and access services/goods, but also to stake their tokens (or other types of tokens) in order to be chosen, or participate in health data validator (HDV) nodes. Additionally, the governance tokens grant members of the DeHI engine and token ecosystem governance and voting rights, as well as entrance into token pools for rewards. In such embodiments, in providing these functions the DeHI module is able to be substantially similar to the token ecosystem module except for the differences described herein.

The EHRNFT is able to be a unit of data representing health records/information about a user, stored on a digital ledger, Chain Arrayed Data Store ("CADS") or blockchain (e.g. MIDC 202 and/or notary chain 206'). Each EHRNFT is able to have a unique identification code and/or metadata that distinguish it from each other tokens. Specifically, the EHRNFT is able to be associated with the digital or physical asset of the user's health records and/or a license to use the health records for a specified purpose. In other words, the EHRNFTs are able to function like cryptographic tokens, but are not mutually interchangeable, and so are not fungible. As a result, the EHRNFTs enable users to license, sell, trade or otherwise share access to their health record in a secure manner that they control. It is noted that although the generation and storage of the IDNFT and/or EHRNFT are described herein as being generated on the MIDC 202 of the user, it is understood that other blockchains are able to be used to mint/store/update the tokens including the notary chain 206' and/or other chains described herein. In such implementations the notary chain 206' would be able to be a private chain and/or the health record data and identification data be encrypted for privacy.

In operation, a user first accesses the DeHI module services via downloading the application and/or accessing the website via a user device 104, 106 for creating a new user account. The DeHI module includes a graphical user interface (as provided by the application/website on the device) that enables the user to then establish a user account (e.g. creates a new username, password and/or biometric data associated with the user).

This generation of a user account is able to be performed by and or uses the same method as described above with respect to the registration module. For example, the on-boarding process for each individual by the module is able to comprise the capture of permissioned biometrics (e.g. voice, face and/or other biometric data) from that individual such that the module provides the benefit of dynamically updating a biometric lock specific to each user. This biometric lock creation functionality and/or the subsequent use thereof in order to verify a user's identity is able to be substantially similar to U.S. patent application Ser. No. 17/025,924, filed Sep. 18, 2020 and entitled "DYNAMIC BIOMETRIC IDENTITY VERIFICATION SYSTEM, METHOD AND DEVICE," which is hereby incorporated by reference. This also allows the platform to uniquely verify that the EHR owning individual is the only party that ultimately controls and their Private Personal Information and/or health data at all times. Additionally, using the privacy compliance module and/or the same method as discussed above, during the initial on-boarding process for an individual, the DeHI module is able to capture all appropriate privacy and regulatory permissions (e.g. HIPPA) to allow the health data to be legally collected and/or shared with a medical provider or other third party, and with the user's prior knowing opt-in permission. In particular, as described above, the system allows such sharing to be zero-trust, fully automated and regulatory law compliant.

As an example, first time users (or their parents where applicable under data privacy law) are able to download the DeHI application (and/or platform 102 application) onto one or more of their devices 104, 106 (e.g. smart phones). Using the application, the user is able to register on the platform 102 which geo-locates the users while ensuring all data and regulatory compliance rules are adhered to and user permissions are knowingly obtained for any data dissemination to the relevant parties or third-parties with the users knowing opt-in permission. Finally, the application (and/or platform) is able to validate the user's identification (e.g. image of their driver's license or valid school and/or parental ID) compared to a live captured facial image along with other biometric data such as voice data) to create a personal biometric lock for the user that only they will be able to unlock thereby protecting their personal data/information and health data (and enabling future verifiable user identification when using the engine/application).

After the registration process is complete, the module is able to convert the collection of the biometric and/or other account data into an identifying non-fungible token (IDNFT) (e.g. including a hash of the collected data as a unique identifier of the token) and store/post the IDNFT as a transaction (e.g. on a single block) on the MIDC 202 of the user on the platform 102 (wherein the MIDC 202 for the user is newly generated during the registration process in the same manner as described above if not already existing). At the same time, the DeHI module (as implemented by the graphical user interface on the website/application) is able to ask permission to collect the user's electronic health records, and upon receiving permission input from the user, the module collects (e.g. via downloads from other databases, input files uploaded by the user, manual health record input from the user or other parties) the records and converts this electronic health record data into another electronic health record non-fungible token (EHRNFT) that is also stored/posted as a transaction (e.g. as a single block) on the MIDC 202 of the user.

The creation of the ID and EHR NFTs is able to comprise generating a unique identifier for the NFT (e.g. a hash or other mathematical result of input the dataset) to be stored with the dataset as a block (e.g. single transaction block on the blockchain). In some embodiments, all of the collected health records (e.g. from multiple different sources) are combined into a single dataset that is used to generate the EHRNFT for the user. Alternatively or in addition, separate EHRNFTs are able to be created for separate portions of the user EHRs. In some embodiments, the module, via its graphical user interface, provides the user with a list of the collected health records and enables a user to generate one or more EHRNFTs by selecting some or all of the collected health records to include within each EHRNFT. Each of the EHRNFTs are able to comprise a unique identifier (e.g. a hash of the dataset) along with the selected associated owner health information (e.g. anonymized as stored on the notary chain) and/or other block data (e.g. timestamp, an identifier of the previous block, and/or other data). Similarly, each of the IDNFTs are able to comprise a unique identifier (e.g. a hash of the dataset) along with associated owner identification information (e.g. anonymized as stored on the notary chain) and/or other block data (e.g. timestamp, an identifier of the previous block, and/or other data).

In some embodiments, the module enables a user to select that their EHRNFT to be fully anonymized before being shared, such that the anonymous EHRNFT is able to be shared with insurance companies or other entities for data collection purposes without exposing the identity of the user. In such embodiments, the anonymization is able to comprise replacing the identifying data with an alphanumeric code (as describe above with respect to user PPI stored on the MIDCs 202). In some embodiments, digital certificates of authenticity (DCoA) are able to be created for the NFTs (EHR NFT and/or IDNFT), and these DCoAs are able to be posted onto the notary blockchain of the platform (e.g. upon validation of the transaction). In some embodiments, each of the EHRNFTs are linked to the IDNFT of the user/user account when they are minted/created. In particular, in some embodiments the IDNFT is married/linked to the EHRNFT by including a pointer or link in the IDNFT (e.g. in block storing the IDNFT) that points to an address of where the EHRNFT is stored (e.g. the address or block identifier of the block on the MIDC where the EHRNFT is stored).

Once the ID and EHR NFTs are created on the platform 102, the personal private information and other data stored thereon is able to be input, maintained, updated, and removed on the platform 102 (as an NFT) in compliance with all relevant data privacy and regulatory laws. Specifically, the module is able to utilize a data privacy and regulatory law compliance function (e.g. via the privacy module) that geo-locates users and/or companies and applies the necessary data and regulatory law protections associated with that location and/or that person. For example, as described above, the platform is able to provide on-chain private personal information storage as well as an alternative off-chain database management system, that complies with General Data Protection Regulation (GDPR), California Consumer Privacy act (CCPA) and other data privacy laws, by only utilizing de-identified, encrypted, pseudoanonymized and/or fully anonymized user data to record data/transactions (e.g. including the IDNFT and/or EHRNFT) while securely storing the native user data separate from the transaction ledgers/blockchains such that erasure is able to be effectuated upon demand by the removal of the stored native user data thereby anonymizing the data recorded on the blocks having the associated transactions. Deletion of an individual's data, via deletion of their MIDC 202 on the system 100—which contains all their PPI in one place—irrevocably deletes the data and any prior link between that data and any natural person fully ensuring full and total compliance with global data privacy law.

Updates to the identification and/or medical health records included in the ID and/or EHR NFTs are able to be effectuated by minting and posting new ID and/or EHR NFTs to the user's MIDC 202 such that the NFT associated with the latest block reflects the updated identification and/or medical health records of the user (with the previous tokens now being outdated). In some embodiments, the DeHI module automatically periodically prompts (e.g. sends reminders) the user to update their identification and/or medical health records. Alternatively or in addition, the user is able to initiation an update process.

Further, after the one or more EHRNFTs have been generated/minted and posted on the MIDC 202 of the user (and/or the associated DCoA is posted on the notary blockchain 206'), the DeHI module enables the user to identify one more entities/providers (e.g. doctors, medical providers) that the users want to provide with access to the stored EHRNFTs. In some embodiments, the module enables the user to manually input or select from a provided list information: identifying the requesting entity (e.g. an entity device identifier, entity website, entity email address, company name, doctor name, doctor license number, insurance name, insurance number, and/or other identifying information); identifying the requested use (e.g. purpose, duration, scope, compensation and/or other use characteristics); and/or other information.

Alternatively, or in addition, the engine is able to receive electronic EHR data requests from the entities themselves (e.g. via user devices 104, 106) and either automatically or upon confirmation from the user provide access to the requested EHRNFTs including the EHR to the entities. In particular, in such embodiments in response to receiving a request message identifying a user/user account, the DeHI module provides a confirmation request message to the user enabling the user to allow or deny access to the requested EHRNFTs. If the requests are denied, the DeHI module provides a denial message to the requesting entity (e.g. device or account) indicating that the request was denied. If the requests are allowed, the DeHI module is able to provide access to the requested EHRNFTs to the requesting entity. These request messages are able to include information: identifying the requesting entity (e.g. an entity device, company name, doctor name, doctor license number, insurance name, insurance number, and/or other identifying information); identifying the requested EHRNFT(s) (e.g. the unique token identifier of the EHRNFT(s), the unique identifier of the user/user account on the platform, identification of the block storing the EHRNFT(s) and/or other token identifying information); identifying the requested use (e.g. purpose, duration, scope, compensation and/or other use characteristics); and/or other information. In some embodiments, the entity is able to submit the request message without an account or with a guest account by accessing the platform website and utilizing a request function. Alternatively or in addition, the entity (e.g. doctor, hospital, insurance provider, researcher, and/or other entity) must first create an entity/provider account using the registration function described above in order to submit a request message. For example, the entity is able to download/access the DeHI module (e.g. in the form of an application and/or website), create a provider account, and upon agreeing to a fee agreement, request access to one or more EHRNFTs including the desired patient records.

Subsequently, after the user finishes indicating one or more entities they wish to share their EHR with and/or the user grants access to the records (either entered into the user interface in response to a confirmation message or enabled prior to the request such that confirmation is unnecessary), the DeHI module provides the entity access to the permissioned EHRNFTs associated with the user. The entity is thereby provided access to the needed health records in a simple and secure manner. In some embodiments, the DeHI module provides access to the EHRNFTs in the same manner as and/or with the authentication module described above.

In addition to (or as a condition of) enabling the request for NFT health records, the DeHI module graphical user interface also enables the provider accounts to submit payments for their record usage/access and to submit health record update information. Specifically, for payment, the module displays a current outstanding payment due balance to the providers and enables the providers to submit payment information for paying the balance. The module is then able to automatically distribute some or all of the payment amount to the corresponding user accounts and/or the platform itself (e.g. using a smart contract associated with the EHRNFTs and/or provider account). For example, the module is able to distribute fungible platform tokens, fiat currency and/or other methods of payment to the user account and/or platform (e.g. using payment information submitted by the user when creating the user account). In some embodiments, each of the EHRNFTs are able to be rented to the provider accounts for a predefined period for a predefined amount (e.g. as defined in a smart contract associated with the EHRNFT operated by the module), wherein once the period expires the module removes access to the EHRNFTs until the provider pays for another rental period to access the EHRNFTs (and/or submits another EHR request to the user).

In order to enable providers/entities to update user's EHRs, upon receiving a request to submit health record update information, the DeHI module provides an information upload and/or editing function wherein upon submission by the provider, the module generates a new updated EHRNFT reflecting the changes to the health record for the user that is added to the MIDC 202 (and/or the DCoA added to the notary blockchain 206") in the same manner as user updates described above. The module is also able to update the EHRNFTs for the user automatically, periodically and/or upon request by the user, wherein after each update a new EHRNFT is generated and posted on the MIDC 202 (and/or the DCoA added to the notary blockchain 206'). The IDNFTs are able to be similarly updated when the user submits or is required to submit new user account data.

Figure 13:
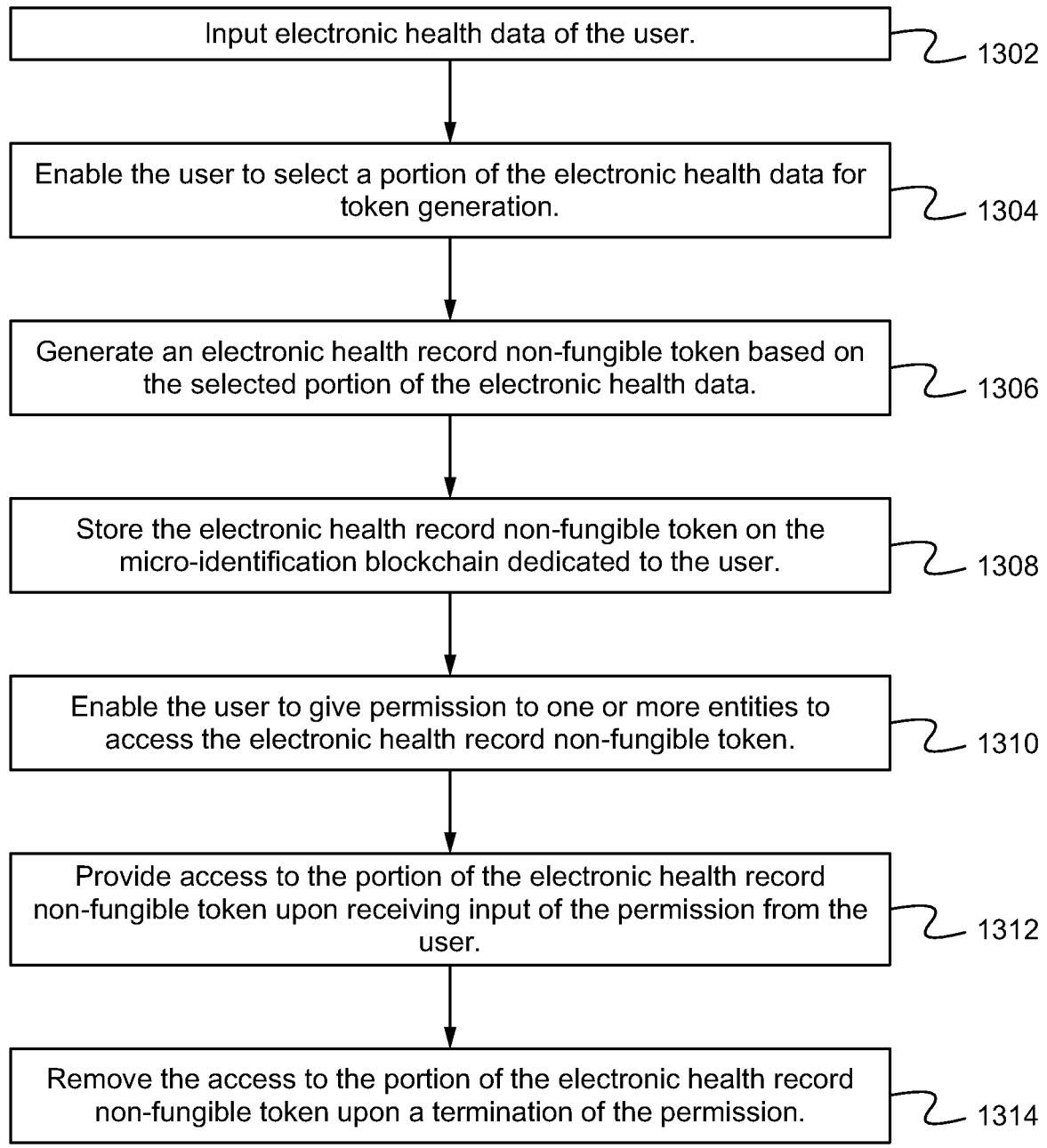
FIG. 13 illustrates a method of operating the DeHI module according to some embodiments.

FIG. 13 illustrates a method of implementing the DeHI module according to some embodiments. As shown in FIG. 13, the DeHI module inputs electronic health data of the user at the step 1302. This inputting is able to be in the form of downloading data from $3^{rd}$ party sources (e.g. websites, applications and/or other network accessible locations), uploads from a user device (e.g. scanned documents, stored files and/or other electronic health data) and/or memory (e.g. universal serial bus drive, external hard drive or other type of memory) and/or manual input of health data from the user via the module user interface (e.g. text input of name, age, sex and/or other health related data via a text box or other data input elements well known in the art). In particular, in some embodiments the DeHI module provides prompts that ask the user to enter or upload required information and/or identify the 3$^{rd}$ party sources where the information can be downloaded by the module.

The module enables the user to select a portion of the electronic health data for token generation at the step 1304. In particular, after all of the electronic health data has been collected, the using a token generation function the module enables the user to indicate a number of tokens they wish to create and what portions of the electronic health data they would like to be a part of each of those tokens. Thus, as user is able to make a first token with all of the data, a second token with only a subset of the data, and any number of tokens with any desired portion of the data. Thus, the method provides the improvement of enabling the user to be able to make customized tokens with varying scopes of health data included such that a token with a first set of data is able to be shared with one party and a token with a second set of data is able to be shared with another party.

Upon completion of the selection by the user, for each of the selected portions of the health data, the module generates/mints an electronic health record non-fungible token based on that portion of the electronic health data at the step 1306. The module then stores the generated EHRNFTs on the micro-identification blockchain 202 dedicated to the user at the step 1308. As described above, each token is able to be stored on a single block separate from any other existing blocks of the micro-identification blockchain 202. The DeHI modules enables the user to give permission to one or more entities to access one or more of the stored EHRNFTs at the step 1310. In particular, as described above, a user is able to specify one or more entities as having permission (e.g. their doctor or insurance company) and/or the entities are able to request permission which the module is able to require confirmation of permission from the user (or prior indication of indefinite permission from the user) before granting access to the EHRNFTs requested. Additionally, in some embodiments the module enables the user to specify a rate or charge for use of the EHRNFTs, a scope of use and/or a duration of use for that entity (or all entities). For example, the module enables the user to specify a flat fee of $100 for 6 months of access to the EHRNFT or a rate of $5 per month with a max duration of one year or an indefinite duration (e.g. until the user manually removes their permission).

Once permission has been determined as being given, the module provides access to the portion(s) of the EHRNFT(s) for which the permission was given at the step 1312. If it is determined that permission is not given, the module is able to send an access denial message to the entities requesting access and/or removing any access privileges to those EHRNFT(s) from the accounts of those entities on the platform 102. Subsequently, the module removes the access to the portion(s) of the EHRNFT(s) upon a termination of the permission at the step 1314. For example, if the duration of the permission was not indefinite and expired or if the required payment by the entity was not made or if the user manually indicates that permission has been revoked. Thus, by implementing EHRNFTs, the method provides the improvement of enabling users to maintain, control and profit from their electronic health records as well as enabling providers and/or other entities to easily access the user's health records.

In some embodiments, the method is able to further comprise the entities using the DeHI module to transmit a heath record request message(s) to the user/user account/user device when they are seeking access to the user's latest health records. The DeHI module is able to then determine if access was given previously by the user that is still valid (e.g. has not been terminated due to duration expiration, failure of payment or user revocation) or if a current permission needs to be given by the user. If a current valid permission still exists, the module is able to give the entities access to the request tokens until the permission terminates. If permission is still required (e.g. confirmation from user needed, payment need and/or other requirement), the module is able to request the conditions needed for permission (e.g. request permission from user and/or request payment from entity), provide access if the conditions are met and deny access to the tokens if they are not met. In some embodiments, enabling the user to give permission to one or more entities to access one or more of the EHRNFT(s) comprises displaying a set of available entities to the user via the module GUI and receiving selection by the user of the one or more entities from the set.

In some embodiments, the method further comprises the module enabling input of updated electronic health data, enabling the user to optionally select another portion of the updated electronic health data for token generation, generating an updated EHRNFT based on the another portion of the updated electronic health data if selected or based on the original portion (as updated), and storing the another EHRNFTs on the micro-identification blockchain 202 dedicated to the user on separate blocks (thereby replacing the previous outdated EHRNFTs). Further, in some embodiments the DeHI module enables the entities that currently have permission to access the EHRNFTs to similarly input updated electronic health data of the user and then generate a new EHRNFT to replace the outdated EHRNFT based on the input electronic health data in the same manner as with a user, but without the entity having the option to select another portion. In some embodiments, the EHRNFT minted is itself able to be dynamically updated to accommodate new or changed data for the individual and their health treatment and/or records.

In some embodiments, the method further comprises inputting biometric data, identification data and/or other types of user account data (as described above) during a registration process. In such embodiments, the module is able to convert the collection of the biometric and/or other account data into an identifying non-fungible token (IDNFT) and store/post the IDNFT as a transaction on the MIDC 202 of the user on the platform 102. In some embodiments, the method further comprises anonymizing the EHR of one or more of the tokens such that they can be shared with one or more of the entities anonymously.

Token Ecosystem Function

In some embodiments, the DeHI module is able to utilize a token ecosystem function substantially similar to the functioning of the token ecosystem module described above with the ecosystem supporting the recording of the EHRNFT DCoA transactions on the notary chain 206'. Specifically, as described in detail in the token ecosystem module section above, when health data is collected, stored and/or updated using the engine/module as described above, the resulting health data transaction is recorded on the MIDC 202 of the user and the platform's secure notary substrate blockchain 206' including a digital certificate of authentication (DCoA). Subsequently, a signature of these DCoAs and the transactions is able to be sent as batches to a selected one of the health data validator (HDV) nodes of a sidechain of the substrate, which confirms each of the transaction/signatures are valid on the sidechain. The confirmed transactions/signatures are then able to be flushed to a parachain or parathread chain (e.g. Polkadot parachain or parathread chain) where they are added for future use in presenting user health data indicated by the transactions and certified by the DCoAs.

Additionally, within the platform token ecosystem, the gas for recording each of the transactions and/or providing the DCoA on the platform substrate blockchain and/or MIDC is paid for using the fungible platform's tokens or some other traditional payment method (e.g., credit card, PayPal, wire transfer, ACH, debit card or some other third party cryptocurrency). After the transaction is completed and authenticated by the selected HDV node on the sidechain, part of this gas (i.e. platform tokens) is bought back by the platform using a second cryptocurrency token (e.g. DOT token). This DOT token is able to provide secondary gas for writing the final blocks to the parachain (e.g. Polkadot parachain) using a network protocol that allows arbitrary data and tokens to be transferred across blockchains (e.g. Polkadot). The remainder of the first gas is able to be paid back to stakers of the HDV node that authenticated the transaction/DCoA on the sidechain as a reward. In some embodiments, the engine/module further enables stakers to participate in governance voting operations.

Advantages

The system 100 described herein have numerous advantages. In particular, the system 100 provides the advantage of enabling a high throughput of transactions recorded on the central public/private hybrid blockchain, or a central private-permissioned blockchain, without sacrificing the immutability of the blockchain by utilizing a posting of transactions with a proof of transaction consensus before any full node consensus protocol combined with using separate single transaction blocks for each transaction such that errors can be corrected with subsequent blocks. Further, it provides the advantage of protecting against chain poisoning by implementing an anti-poisoning module that prevents poisoned blocks from being posted to the blockchain. Additionally, the system 100 provides the increased security of micro-identification chains instead of databases which are susceptible to breaches. Moreover, the system 100 provides a compliance module that automatically complies with privacy regulations for all on-boarded user PPI. Also, it provides a block explorer module that enables databases to easily be imported into the MIDC arrays. Further, the system 100 enables the users to remain in complete control of their personal data without disrupting the immutability of the notary/transaction blockchain by including a ripcord feature (to effectuate erasure or deletions) that fully de-identifies and/or anonymizes any user who wishes to discontinue using the service.

As described above, the MS module provides the benefit of being able to uniquely verify that the individual (employee, teacher, student, etc.) presenting results of a test is the actual person taking the test, ensuring the "chain of custody" of the test from inception through results, and ensuring that the individual taking the test is the only party that ultimately controls and their Private Personal Information and/or health data at all times. Additionally, the system's use in some embodiments of daily inexpensive, rapid, covid-19 active virus antigen tests—combined with the real time updating of attestations and covid-19 health status/infectiousness of individuals—the system is able to alert schools, businesses, permissioned third parties and individuals and prevent any covid-19 infectious individuals from entering the physical workplace before they even leave their home. In this regard the system functions as a covid-19 "early warning system."

Further, the DeHI module provides an improvement over existing health systems by enabling users to securely share their health data with health providers as needed and/or license access to their health data to health providers and/or other entities in order to monetize their health data. Additionally, the use of NFTs enables the user to customize which health data is combined and provided for use by the entities while also securely tying control of each of the EHRNFTS to the user themselves. Moreover, the module provides the improvement of enabling the providers themselves to request and/or update the EHRNFTs such that accurate health data is able to be consistently accessed and/or kept current.

The present invention has been described in terms of specific embodiments incorporating details to facilitate the understanding of principles of construction and operation of the invention. Such reference herein to specific embodiments and details thereof is not intended to limit the scope of the claims appended hereto. It will be apparent to those skilled in the art that modification may be made in the embodiments chosen for illustration without departing from the spirit and scope of the invention. For example, in some embodiments the application includes a deadbolt function that provides real-time feedback on the smart contracts that the blockchain operating system generates as well as providing alerts on suspicious activity in order to prevent the activity from taking place. In some embodiments, the transfer of tokens and/or other moneys described herein between the operating systems/blockchains (e.g. for effectuating payments and/or issuing pre-order tokens) is effectuated used the pegged sidechains as a method of transferring the tokens between the blockchains/operating systems. As used herein, a user, buyer and/or seller is able to be any entity (e.g. person, business, fund, government entity) that is able to be due compensation on the system 100 (e.g. for a transaction and/or other feature). Specifically, even if they are not a part of the process, the entities are able to have accounts on the system such that the system is able to compensate them as necessary (e.g. as indicated in the smart contracts).

Further, although the functions of the platform 102 and/or operating system 206 have been divided according to an exemplary number of modules having an exemplary subset of the functions of the platform 102, it is understood that other divisions and/or numbers of modules are contemplated (with the overall functionality of the platform 102 being the same), but omitted for the sake of brevity. Further, it is understood that the functions described herein as being performed by operating systems, applications, modules, graphical user interfaces and/or other types of software are performed via the software being stored on a non-transitory computer readable memory of and executed by one or more processors of one or more of the electronic devices described herein (in combination with or separately from other hardware such as wireless transceivers). Similarly, it is understood that functions described herein as being performed by devices, servers, blockchains, MIDCs and/or other types of electronic devices are performed via non-transitory computer readable memory and one or more processors of the electronic devices storing and executing one or more operating systems, applications, modules, graphical user interfaces and/or other types of software (in combination with or separately from other hardware of the electronic devices such as wireless transceivers). As used herein, the term "transaction" is able to also refer to an "object" and vice versa.

What is claimed is:

1. An electronic health record blockchain platform for sharing electronic health records of a plurality of users having accounts on the platform, the platform comprising:
a non-transitory computer-readable memory cluster storing a micro-identification blockchain array formed by a stack of a plurality of micro-identification blockchains, wherein at least one of the micro-identification blockchains is dedicated to a user of the users; and
a user device including a user device processor and a user device non-transitory memory storing a health application, wherein when executed by the user device processor the health application is operable to:
input electronic health data of the user;
enable the user to select a portion of the electronic health data for token generation;
generate an electronic health record non-fungible token (EHRNFT) based on the selected portion of the electronic health data, the EHRNFT including a token identifier and the selected portion;
store the EHRNFT on the micro-identification blockchain dedicated to the user as a single block separate from any existing blocks of the micro-identification blockchain;
enable the user to give permission to one or more entities to access the EHRNFT;
provide access to the portion of the EHRNFT upon receiving input of the permission from the user; and
remove the access to the portion of the EHRNFT upon a termination of the permission.

2. The electronic health record blockchain platform of claim 1, wherein the electronic health data includes one or more current medical conditions of the user and a medical history of the user.

3. The electronic health record blockchain platform of claim 2, further comprising an entity device including an entity device processor and an entity device non-transitory memory storing the health application, wherein when executed by the entity device processor the health application is operable to:
enable a provider to transmit a heath record request message to the user device, the health record request message including an identifier of the user and the token identifier; and
enable the provider to submit payment to the user for access to the EHRNFT identified by the token identifier.

4. The electronic health record blockchain platform of claim 3, wherein the enabling the user to give permission to one or more entities to access the EHRNFT comprises communicating a permission confirmation message to the user on the user device in response to receiving the health record request message.

5. The electronic health record blockchain platform of claim 3, wherein the enabling the user to give permission to one or more entities to access the EHRNFT comprises displaying a set of available entities to the user on the user device and receiving selection by the user of the one or more entities from the set.

6. The electronic health record blockchain platform of claim 3, wherein the termination of the permission comprises an expiration of a rental period associated with the EHRNFT.

7. The electronic health record blockchain platform of claim 6, wherein the health application is operable to extend the rental period upon receipt of payment from the provider.

8. The electronic health record blockchain platform of claim 7, wherein when executed by the user device processor the health application is operable to:
enable input of updated electronic health data;
enable the user to select another portion of the updated electronic health data for token generation;
generate an updated EHRNFT based on the another portion of the updated electronic health data, the updated EHRNFT including another token identifier and the another portion; and
store the another EHRNFTs on the micro-identification blockchain dedicated to the user on another separate block.

9. The electronic health record blockchain platform of claim 8, wherein when executed by the entity device processor the health application is operable to enable the provider to input the updated electronic health data.

10. The electronic health record blockchain platform of claim 1, wherein when executed by the user device processor the health application is operable to:
enable the user to select one or more additional portions of the electronic health data for token generation;
generate an additional EHRNFT for each of the additional portions based on the additional portion of the electronic health data, the additional EHRNFTs each including an additional token identifier and the additional portion; and
store each of the additional EHRNFTs on the micro-identification blockchain dedicated to the user on a separate additional block.

11. The electronic health record blockchain platform of claim 1, wherein the token identifier is a hash of the selected portion of the electronic health data.

12. A non-transitory computer-readable medium of a device storing a health application, wherein when executed by a device processor the health application is operable to:
input electronic health data of the user;
enable the user to select a portion of the electronic health data for token generation;
generate an electronic health record non-fungible token (EHRNFT) based on the selected portion of the electronic health data, the EHRNFT including a token identifier and the selected portion;
store the EHRNFT on a micro-identification blockchain dedicated to the user as a single block separate from any existing blocks of the micro-identification blockchain, the micro-identification blockchain stored on a non-transitory computer-readable memory cluster;
enable the user to give permission to one or more entities to access the EHRNFT; provide access to the portion of the EHRNFT upon receiving input of the permission from the user; and
remove the access to the portion of the EHRNFT upon a termination of the permission.

13. The non-transitory computer-readable medium of claim 12, wherein the electronic health data includes one or more current medical conditions of the user and a medical history of the user.

14. The non-transitory computer-readable medium of claim 13, wherein when executed by the device processor the health application is operable to:

enable a provider to transmit a heath record request message to the user, the health record request message including an identifier of the user and the token identifier; and enable the provider to submit payment to the user for access to the EHRNFT identified by the token identifier.

15. The non-transitory computer-readable medium of claim 14, wherein the enabling the user to give permission to one or more entities to access the EHRNFT comprises communicating a permission confirmation message to the user on the user device in response to receiving the health record request message.

16. The non-transitory computer-readable medium of claim 14, wherein the enabling the user to give permission to one or more entities to access the EHRNFT comprises displaying a set of available entities to the user on the device and receiving selection by the user of the one or more entities from the set.

17. The non-transitory computer-readable medium of claim 14, wherein the termination of the permission comprises an expiration of a rental period associated with the EHRNFT.

18. The non-transitory computer-readable medium of claim 17, wherein the health application is operable to extend the rental period upon receipt of payment from the provider.

19. The non-transitory computer-readable medium of claim 18, wherein when executed by the device processor the health application is operable to:
enable input of updated electronic health data;
enable the user to select another portion of the updated electronic health data for token generation;
generate an updated EHRNFT based on the another portion of the updated electronic health data, the updated EHRNFT including another token identifier and the another portion; and
store the another EHRNFTs on the micro-identification blockchain dedicated to the user on another separate block.

20. The non-transitory computer-readable medium of claim 19, wherein when executed by the device processor the health application is operable to enable the provider to input the updated electronic health data.

21. The non-transitory computer-readable medium of claim 12, wherein when executed by the device processor the health application is operable to:
enable the user to select one or more additional portions of the electronic health data for token generation;
generate an additional EHRNFT for each of the additional portions based on the additional portion of the electronic health data, the additional EHRNFTs each including an additional token identifier and the additional portion; and
store each of the additional EHRNFTs on the micro-identification blockchain dedicated to the user on a separate additional block.

22. The non-transitory computer-readable medium of claim 12, wherein the token identifier is a hash of the selected portion of the electronic health data.

23. A method of sharing electronic health data of a plurality of users using a micro-identification blockchain array formed by a stack of a plurality of micro-identification blockchains, wherein at least one of the micro-identification blockchains is dedicated to a user of the users, the method comprising:

with a user device having a processor and a non-transitory computer-readable memory storing a health application:
inputting electronic health data of the user;
enabling the user to select a portion of the electronic health data for token generation;
generating an electronic health record non-fungible token (EHRNFT) based on the selected portion of the electronic health data, the EHRNFT including a token identifier and the selected portion;
storing the EHRNFT on the micro-identification blockchain dedicated to the user as a single block separate from any existing blocks of the micro-identification blockchain;
enabling the user to give permission to one or more entities to access the EHRNFT;
providing access to the portion of the EHRNFT upon receiving input of the permission from the user; and
removing the access to the portion of the EHRNFT upon a termination of the permission.

24. The method of claim 23, wherein the electronic health data includes one or more current medical conditions of the user and a medical history of the user.

25. The method of claim 24, further comprising, with an entity device storing the health application:
enabling a provider to transmit a heath record request message to the user device, the health record request message including an identifier of the user and the token identifier; and
enabling the provider to submit payment to the user for access to the EHRNFT identified by the token identifier.

26. The method of claim 25, wherein the enabling the user to give permission to one or more entities to access the EHRNFT comprises communicating a permission confirmation message to the user on the user device in response to receiving the health record request message.

27. The method of claim 25, wherein the enabling the user to give permission to one or more entities to access the EHRNFT comprises displaying a set of available entities to the user on the user device and receiving selection by the user of the one or more entities from the set.

28. The method of claim 25, wherein the termination of the permission comprises an expiration of a rental period associated with the EHRNFT.

29. The method of claim 28, wherein the health application is operable to extend the rental period upon receipt of payment from the provider.

30. The method of claim 29, further comprising with the user device:
enabling input of updated electronic health data;
enabling the user to select another portion of the updated electronic health data for token generation;
generating an updated EHRNFT based on the another portion of the updated electronic health data, the updated EHRNFT including another token identifier and the another portion; and
storing the another EHRNFTs on the micro-identification blockchain dedicated to the user on another separate block.

31. The method of claim 30, wherein when executed by the entity device processor the health application is operable to enable the provider to input the updated electronic health data.

32. The method of claim 23, further comprising with the user device:

enabling the user to select one or more additional portions of the electronic health data for token generation;

generating an additional EHRNFT for each of the additional portions based on the additional portion of the electronic health data, the additional EHRNFTs each including an additional token identifier and the additional portion; and storing each of the additional EHRNFTs on the micro-identification blockchain dedicated to the user on a separate additional block.

33. The method of claim 23, wherein the token identifier is a hash of the selected portion of the electronic health data.

* * * * *